United States Patent
Mandelis et al.

(10) Patent No.: US 9,220,415 B2
(45) Date of Patent: Dec. 29, 2015

(54) SYSTEMS AND METHODS FOR FREQUENCY-DOMAIN PHOTOACOUSTIC PHASED ARRAY IMAGING

(71) Applicants: Andreas Mandelis, Scarborough (CA); Sergey Telenkov, Toronto (CA); Bahman Lashkari, Toronto (CA)

(72) Inventors: Andreas Mandelis, Scarborough (CA); Sergey Telenkov, Toronto (CA); Bahman Lashkari, Toronto (CA)

(*) Notice: Subject to any disclaimer, the term of this patent is extended or adjusted under 35 U.S.C. 154(b) by 407 days.

(21) Appl. No.: 13/660,771

(22) Filed: Oct. 25, 2012

(65) Prior Publication Data

US 2013/0102865 A1  Apr. 25, 2013

Related U.S. Application Data

(60) Provisional application No. 61/551,261, filed on Oct. 25, 2011.

(51) Int. Cl.
*A61B 5/00* (2006.01)
*A61B 5/1455* (2006.01)
*G01N 21/17* (2006.01)
*G01N 21/31* (2006.01)
*G01N 21/39* (2006.01)
*G01N 21/47* (2006.01)
*G03B 42/06* (2006.01)

(52) U.S. Cl.
CPC .......... *A61B 5/0095* (2013.01); *A61B 5/14551* (2013.01); *A61B 5/14552* (2013.01); *A61B 5/7235* (2013.01); *A61B 5/7257* (2013.01); *G01N 21/1702* (2013.01); *G01N 21/314* (2013.01); *G01N 21/39* (2013.01); *G01N 21/4795* (2013.01); *G03B 42/06* (2013.01)

(58) Field of Classification Search
CPC .............................. A61B 5/0095; G03B 42/06
USPC ........................................................ 600/328
See application file for complete search history.

(56) References Cited

U.S. PATENT DOCUMENTS

| | | | |
|---|---|---|---|
| 4,950,897 A | 8/1990 | Mandelis et al. | |
| 5,667,300 A | 9/1997 | Mandelis et al. | |
| 6,584,341 B1 | 6/2003 | Mandelis et al. | |
| 7,045,786 B2 | 5/2006 | Mandelis et al. | |
| 7,525,661 B2 | 4/2009 | Mandelis et al. | |

(Continued)

FOREIGN PATENT DOCUMENTS

WO  WO 2010109205 A2 *  9/2010
WO  WO 2011053931 A2 *  5/2011

OTHER PUBLICATIONS

Aguirre, A. et al., "Coregistered three-dimensional ultrasound and photoacoustic imaging system for ovarian tissue characterization" J. Biomed. Opt. 14(5), 054014-1-9 (2009).

(Continued)

*Primary Examiner* — Katherine Fernandez
*Assistant Examiner* — Katherine McDonald
(74) *Attorney, Agent, or Firm* — Hill & Schumacher

(57) ABSTRACT

Systems and methods of frequency-domain photoacoustic imaging are provided utilizing an ultrasonic phased array probe and intensity modulated optical excitation with coding to improve signal-to-noise ratio. Embodiments employ frequency-domain photoacoustic imaging methodologies such as the photoacoustic radar, coupled with a multi-element ultrasonic sensor array to deliver spatially-resolved correlation images of photoacoustic sources, which may be employed to image optical heterogeneities within tissue-like scattering media.

19 Claims, 14 Drawing Sheets

(56) References Cited

U.S. PATENT DOCUMENTS

| | | | |
|---|---|---|---|
| 8,306,608 B2 | 11/2012 | Mandelis et al. | |
| 2004/0193057 A1* | 9/2004 | Barbato et al. | 600/459 |
| 2005/0150309 A1* | 7/2005 | Beard | 73/861.18 |
| 2005/0168735 A1* | 8/2005 | Boppart et al. | 356/301 |
| 2011/0118571 A1* | 5/2011 | Mandelis et al. | 600/316 |
| 2011/0238002 A1* | 9/2011 | Kurkayev | 604/21 |

OTHER PUBLICATIONS

Niederhauser, J. et al., "Combined Ultrasound and Optoacoustic System for Real-Time High-Contrast Vascular Imaging in Vivo", IEEE Trans. Med. Imag. 24 (4), 436-440 (2005).

Telenkov, S. et al., "Signal-to-noise analysis of biomedical photoacoustic measurements in time and frequency domains", Rev. Sci. Inst. 81, 124901 (2010).

* cited by examiner

SYSTEMS AND METHODS FOR FREQUENCY-DOMAIN PHOTOACOUSTIC PHASED ARRAY IMAGING

CROSS-REFERENCE TO RELATED APPLICATION

This application claims priority to U.S. Provisional Application No. 61/551,261, titled "SYSTEMS AND METHODS FOR FREQUENCY-DOMAIN PHOTOACOUSTIC RADAR PHASED ARRAY IMAGING" and filed on Oct. 25, 2011, the entire contents of which are incorporated herein by reference.

BACKGROUND

The present disclosure is related to biomedical optical imaging methods. More particularly, the present disclosure is related to the noninvasive photoacoustic imaging of tissue vasculature.

The vascular network of the circulatory system is an essential part of living organisms, providing a function that is responsible for transport of nutrients and oxygen to cells and removal of waste products. Blood hemoglobin confined to blood vessels serves as the oxygen carrier and has vital importance for tissue health, healing and cell growth across the human body.

Noninvasive imaging of tissue vasculature may provide important information about the health of an organism, disease development and response to specific therapy administered during treatment procedures. The laser photoacoustic method of vascular imaging relies on optically induced pressure waves in tissue to visualize the position and oxygen content of blood hemoglobin taking advantage of the unique spectral signatures of oxy- and deoxy-hemoglobin. In principle, two- and three-dimensional photoacoustic imaging can be accomplished using a single element ultrasonic transducer mechanically scanned over the region of interest. Unfortunately, this imaging modality is notoriously slow and tedious. Furthermore, the use of large pulsed laser sources operating at slow repetition rates (~10 Hz) makes it difficult or impossible to design and construct portable clinical field imaging photoacoustic systems operating at real-time image formation rates.

SUMMARY

Systems and methods of frequency-domain photoacoustic imaging are provided utilizing an ultrasonic phased array probe and intensity modulated optical excitation with coding to improve signal-to-noise ratio. Embodiments employ frequency-domain photoacoustic imaging methodologies such as the photoacoustic radar, coupled with a multi-element ultrasonic sensor array to deliver spatially-resolved correlation images of photoacoustic sources, which may be employed to image optical heterogeneities within tissue-like scattering media.

Accordingly, in one aspect, there is provided a method of performing photoacoustic imaging within a sample, the method comprising the steps of:
providing an optical beam, wherein a wavelength of the optical beam is selected such that the optical beam is absorbed when directed onto the sample;
generating a reference modulation waveform for modulating the optical beam;
modulating the optical beam according to the reference modulation waveform, thereby obtaining a modulated optical beam;
directing the modulated optical beam into the sample;
detecting, with an ultrasonic transducer array, photoacoustic waves responsively generated within the sample and obtaining a photoacoustic signal from each element of ultrasonic transducer array;
for each element in the ultrasonic transducer array, computing a cross-correlation function based on a Fourier transform of the photoacoustic signal and the reference modulation waveform; and
processing the cross-correlation functions of the array elements and forming a cross-correlation image according to a beamforming algorithm.

In another aspect, there is provided a photoacoustic imaging system comprising:
an optical source for producing an optical beam, wherein a wavelength of the optical source is selected such that the optical beam is absorbed when directed on a sample;
modulating means for modulating the optical source according to a reference modulation waveform and generating a modulated optical beam;
an ultrasonic transducer array configured to detect photoacoustic waves generated in response to absorption of the modulated optical beam and to provide a photoacoustic signal from each element of the ultrasonic transducer array; and
a control and processing unit configured to:
generate the reference modulation waveform;
calculate, for each element of the ultrasonic transducer array, a cross-correlation function based on a Fourier transform of a detected photoacoustic signal and the reference modulation waveform; and
process the cross-correlation functions according to a beamforming algorithm for generating a cross-correlation image.

In another aspect, there is provided a method of measuring a differential photoacoustic signal from a sample, wherein an absorption spectrum of the sample includes an isosbestic point associated with two absorbing species, the method comprising:
providing a first optical beam having a first wavelength, wherein the first wavelength is approximately equal to a wavelength of the isosbestic point;
providing a second optical beam having second wavelength, wherein the second wavelength is different than the first wavelength;
generating a reference modulation waveform;
modulating the first optical beam and the second optical beam according to the reference modulation waveform, thereby obtaining a first modulated optical beam and a second modulated optical beam, wherein the first modulated optical beam and the second modulated optical beam are approximately out of phase;
directing the first modulated optical beam and the second modulated optical beam onto the sample; and
detecting, with at least one ultrasonic transducer, photoacoustic waves responsively generated within the sample and obtaining a differential photoacoustic signal from the at least one ultrasonic transducer.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
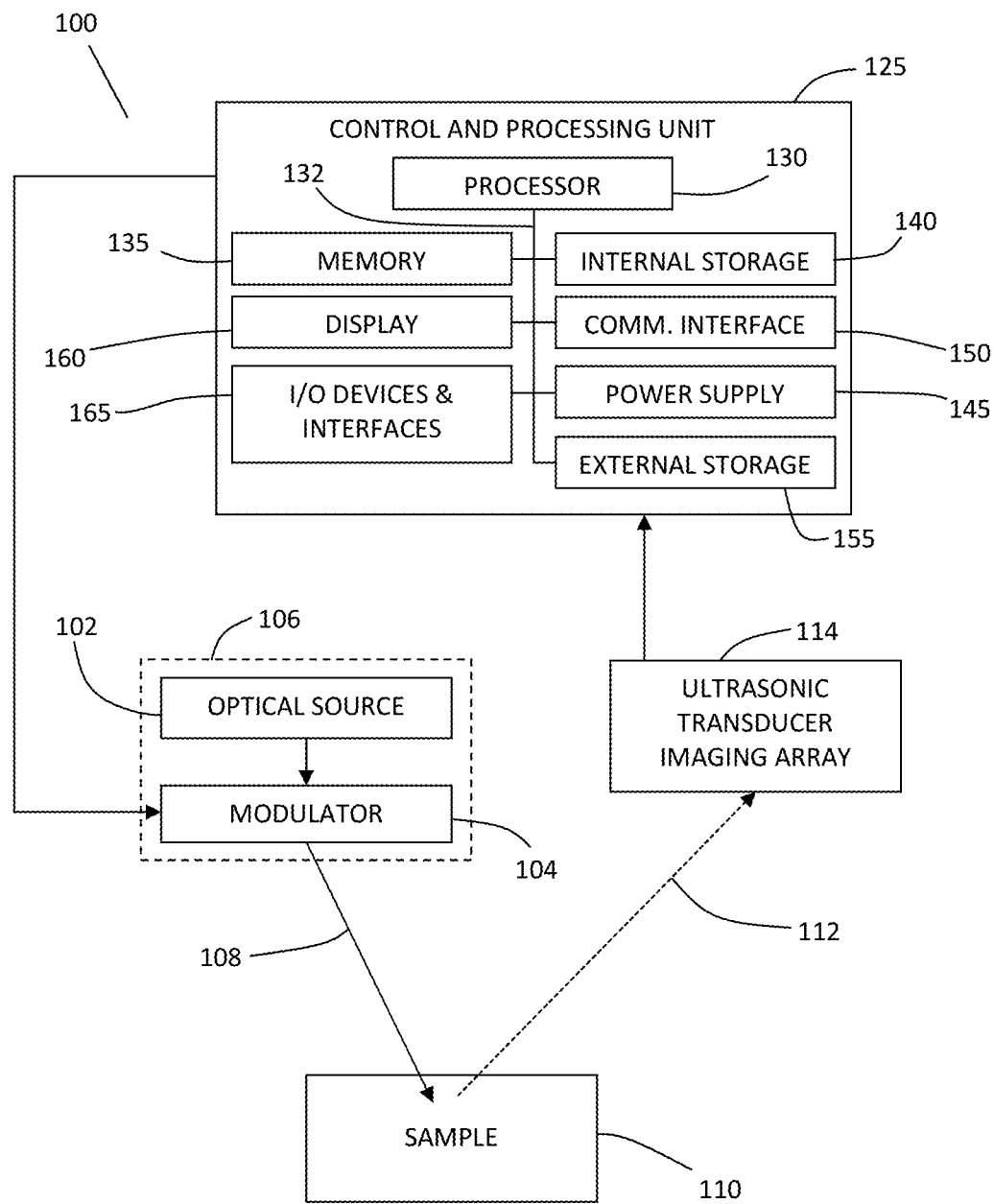
FIG. 1 is a block diagram illustrating an example of a system for performing photoacoustic imaging with a transducer array and correlation image post-processing.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

In the present disclosure, photoacoustic radar imaging methods and systems are provided that employ intensity-modulated continuous wave (CW) laser or pulsed laser source waveforms for acoustic wave generation and an ultrasonic phased array probe for signal acquisition. In selected embodiments, multi-element data collection and image reconstruction are performed using frequency-domain correlation processing followed by digital beamforming, as applied to the correlation data.

Instead of simply using the amplitude of the acoustic pressure directly for image reconstruction, as in known pulsed photoacoustic and ultrasound methods, embodiments of the present disclosure involve the computation of the cross-correlation function of the photoacoustic response with a specific modulation signal (which may be stored in a computer-readable memory). As a result, the reconstructed image represents the spatial distribution of the correlation function, which can be related to the amplitude of the photogenerated acoustic waves.

Three main features differentiate the methods described below from the conventional approach to photoacoustic imaging utilizing fixed-repetition-rate short pulse (nanosecond) laser sources: (a) use of intensity-modulated CW laser beam(s) modulated by modulation signals such as linear and nonlinear frequency sweeps, variable repetition rate pulse trains or phase-manipulated signal with specific coding algorithm (Barker, Golay, etc.). or through coded modulation (Golay, Barker or other types of codes); (b) the introduction of customized optical waveforms ("waveform engineering"), which allows for an improved and/or optimized signal-to-noise ratio through a combination of high-peak-power optical pulse trains and linear (or non-linear) frequency or coded waveforms, resulting in enhanced signal-to-noise ratio (SNR) over fixed-repetition-rate pulses; and (c) a correlation signal processing method that allows one to increase (SNR) in addition to (b) and offers axial resolution improvement through pulse compression (wide bandwidth approach) or spectral sidelobe suppression (narrow bandwidth approach), respectively.

Therefore, in embodiments provided herein, the signal-to-noise ratio (SNR) and axial resolution can be increased relative to that of fixed-repetition-rate short pulse laser sources by modulating or coding the laser source in a certain pattern and compressing the frequency spectrum to a narrow peak, and by obtaining pulse compression into a narrow peak through cross-correlation signal processing.

Although the use of CW laser sources for photoacoustic imaging, in particular, inexpensive sources such as laser diodes, is very attractive for the design of portable clinical instrumentation, typically, the amplitude of acoustic waves generated by such sources is small. Accordingly, embodiments of the present disclosure employ signal processing methods to detect the photoacoustic response in the presence of much higher noise (than the amount of noise present when using fixed-repetition-rate short pulse laser sources), as discussed above and described further below. An approach to photoacoustic detection, as contemplated in selected embodiments provided herein, employs relatively long (millisecond-timescale) optical excitation with a specific modulation pattern and signal compression to increase SNR. The specific modulation pattern may be a coded waveform having a coding pattern selected to enhance the SNR.

As described further below, signal compression and SNR enhancement may be realized by utilizing a digital matched filter that provides an equivalent of the cross-correlation of the received photoacoustic signals and the laser modulation waveform. The output of the correlation processor implementing the digital matched filter is a narrow signal peak that is observed at the moment when the acoustic delay time due to wave propagation is equal to the delayed reference modulation signal. This type of signal processing can be efficiently realized in frequency-domain using fast Fourier transforms (FFT) and simple product operations applied to complex valued spectra of the recorded signals. This is the principle of signal processing utilized in frequency-domain photoacoustic imaging of optical contrast with high axial resolution. An additional feature of the frequency domain correlation processing is the phase of the correlation function that potentially can be used for imaging instead of, or in addition to, the amplitude information available from the correlation envelope [Ref. Telenkov & Mandelis, Journal of Biomedical Optics 11 (4), 044006_July/August 2006]. This complementary phase information is not available in conventional pulsed photoacoustic method operating exclusively with envelopes of acoustic transients. Although phase can be derived using real and imaginary parts of the complex valued correlation function, the practical use of the phase data for imaging applications is limited by the signal-to-noise ratio (SNR). In order to avoid ambiguities and discontinuities in the images reconstructed using correlation phase, additional signal conditioning (thresholding, interpolation, fitting etc.) is typically employed.

Use of a multi-element transducer array (phased array) for frequency-domain photoacoustic imaging is challenging for two reasons: first due to the low SNR of the recorded signals and, second, because large amounts of photoacoustic raw data must be processed sufficiently fast to enable real-time image display. For high-speed data acquisition and processing, multichannel hardware and parallel software algorithms may be employed, which enable simultaneous processing of multiple data streams.

In one embodiment, following correlation processing of the individual sensor element, the image reconstruction is carried out by using a beamforming algorithm to produce a cross-correlation amplitude sector image in a manner similar to that of conventional B-mode ultrasound. Beamforming algorithms and image reconstruction can be implemented on the correlation data either in time-domain, using for example a delay-and-sum algorithm, or in frequency-domain using phase shifts applied to the correlation Fourier spectrum of the array elements according to the direction of the detection beam. Thus, the resulting image produced by electronic beam steering is, in the present embodiments, a spatially-resolved photoacoustic cross-correlation image. This is a distinct difference between the methods disclosed herein and the methods employed in standard pulsed photoacoustics and conventional ultrasound.

Referring now to FIG. 1, an illustration is provided of an example system 100 for performing photoacoustic array imaging and generating correlation images. System 100 includes optical source 102 for generating an optical beam and optical modulator 104, which may be provided separately, or integrated into a single apparatus or unit 106 (for example, optical modulator 104 may be provided as direct current modulation of a semiconductor laser). Optical source 102 may be any source of electromagnetic radiation with a wavelength consistent with the absorption spectrum of the sample.

For example, the sample may be tissue, in which case the wavelength is tailored to the absorption spectrum of the targeted tissue chromophores. As two examples, a near-IR source with the wavelength in the range 600 nm-1100 nm is suitable for photoacoustic imaging of tissue vasculature due to relatively high absorption of blood hemoglobin and low absorption of surrounding tissues. A near-IR source in the 1200-nm range is optimal for lipid-rich vascular tissue diagnostics. To induce a photoacoustic response, the optical beam 108 is modulated and directed onto sample 110, where the absorbed optical radiation creates temperature oscillations responsible for the generation of photoacoustic waves that propagate 112 and are detected by ultrasound transducer array 114.

Control and processing unit 125, which is described in further detail below, is employed for the control of optical modulator 104 and the processing of signals obtained by imaging array 114. In one embodiment, control and processing unit 125 is configured to generate a reference waveform for modulating the optical beam. Rapid processing may be achieved by a parallel electrical connection between ultrasonic transducer imaging array 114 and control and processing unit 125. Control and processing subsystem 125 receives image data from ultrasonic transducer imaging array 114 and processes the imaging data to determine the correlation image, as described further below. Optical source 106 and modulator 104 include all necessary optical components for the delivery of the optical beam 108 to sample 110. Optical components may include, but are not limited to, imaging and/or focusing components such as lenses, mirrors, optical fibers and optical scanning subsystems. Control and processing subsystem 125 may be integrated with one or more of the other subsystems of system 100.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

FIG. 1 provides an example implementation of control and processing unit 125, which includes one or more processors 130 (for example, a CPU/microprocessor), bus 132, memory 135, which may include random access memory (RAM) and/or read only memory (ROM), one or more internal storage devices 140 (e.g. a hard disk drive, compact disk drive or internal flash memory), a power supply 145, one more communications interfaces 150, external storage 155, a display 160 and various input/output devices and/or interfaces 155 (e.g., a receiver, a transmitter, a speaker, a display, an imaging sensor, such as those used in a digital still camera or digital video camera, a clock, an output port, a user input device, such as a keyboard, a keypad, a mouse, a position tracked stylus, a position tracked probe, a foot switch, and/or a microphone for capturing speech commands).

Data processing speed is an important performance factor for a wide range of uses of a photoacoustic probe, such as in clinical applications. Accordingly, processing and control unit 125 may further include multichannel data acquisition hardware, and processor 130 may be programmed with parallel software algorithms, to support high-speed parallel data acquisition and processing. For example, since frequency-domain photoacoustic imaging typically requires acquisition of millisecond long signals with a sampling rate of tens of megahertz, the resulting matrix of raw data can be quite large. High-speed processing of large data arrays can be achieved using parallel processing hardware with frequency domain signal representation and fast Fourier transforms for rapid correlation processing.

Although only one of each component is illustrated in FIG. 1, any number of each component can be included in the control and processing unit 100. For example, a computer typically contains a number of different data storage media. Furthermore, although bus 132 is depicted as a single connection between all of the components, it will be appreciated that the bus 132 may represent one or more circuits, devices or communication channels which link two or more of the components. For example, in personal computers, bus 132 often includes or is a motherboard.

In one embodiment, control and processing unit 125 may be, or include, a general purpose computer or any other hardware equivalents. Control and processing unit 125 may also be implemented as one or more physical devices that are coupled to processor 130 through one of more communications channels or interfaces. For example, control and processing unit 125 can be implemented using application specific integrated circuits (ASICs). Alternatively, control and processing unit 125 can be implemented as a combination of hardware and software, where the software is loaded into the processor from the memory or over a network connection.

Control and processing unit 125 may be programmed with a set of instructions which when executed in the processor causes the system to perform one or more methods described in the disclosure. Control and processing unit 125 may include many more or less components than those shown.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like.

Figure 2:
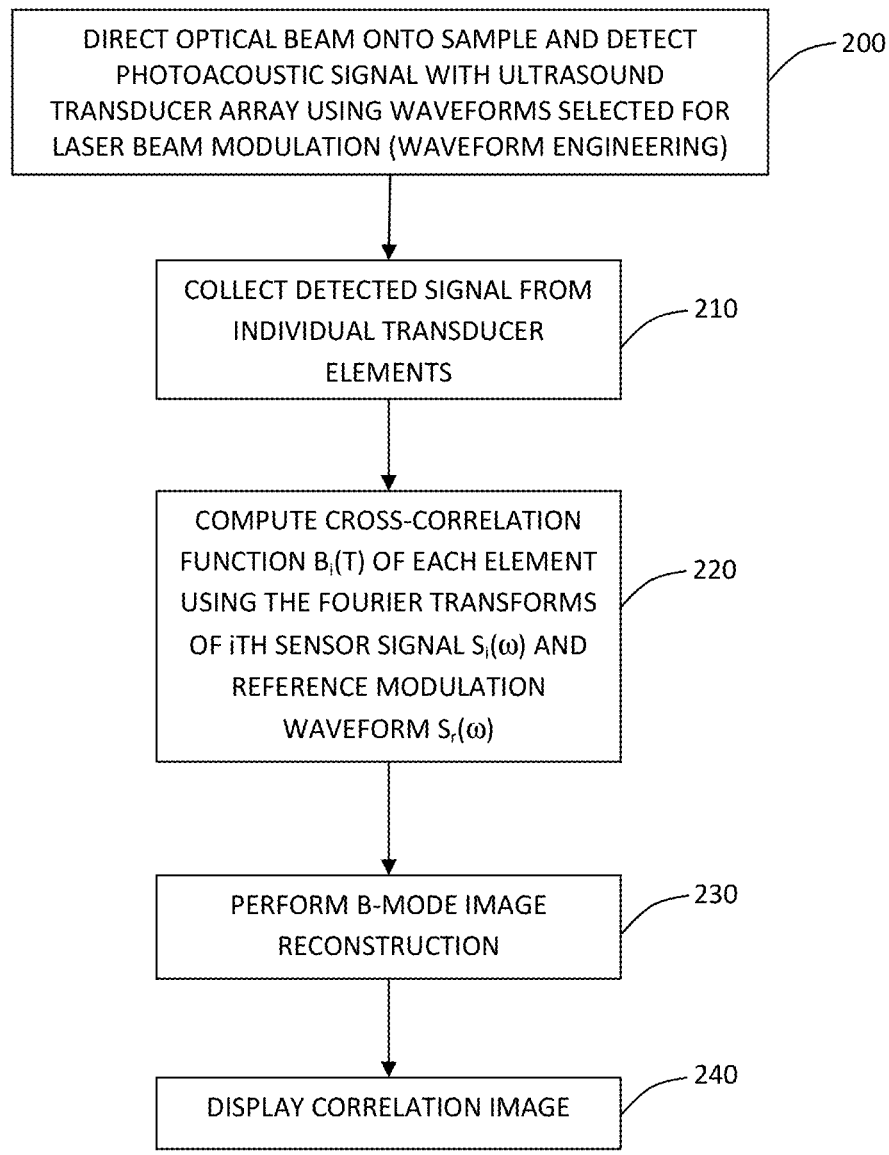
FIG. 2 is a flow chart describing a method of performing array-based photoacoustic imaging in which B-mode image reconstruction is employed.

In one example implementation, signal processing and image formation using the photoacoustic probe is as accomplished as illustrated in the flow chart shown in FIG. 2. In step 200, the modulated laser is directed onto the sample, and a photoacoustic response is generated and detected by the ultrasound transducer array. Additionally, waveform engineering may be applied to improve or optimize photoacoustic radar signal generation and SNR, as discussed below. The detected signal data are then collected from the transducer elements in step 210 and stored for further processing a computer-readable memory for subsequent processing.

As shown at step 220, the complex-valued cross-correlation function $B_i(t)$ of each element (represented by index i) is computed using the Fourier transforms of the i-th sensor signal $S_i(\omega)$ and the reference modulation waveform $S_r(\omega)$. The cross-correlation function as a function of time $B_i(t)$ can be computed using the inverse Fourier transform as shown in Eq. (1):

$$B_i(t) = \frac{1}{2\pi}\int_{-\infty}^{+\infty} S_r^*(\omega)S_i(\omega)e^{i\omega t}d\omega \qquad (1)$$

The subsequent stage of signal processing, shown at step 230, involves B-mode image reconstruction, which is achieved by forming multiple receiving beams electronically steered over the area of interest. Although those skilled in the art will be aware that there are many beamforming methods available, in the standard delay-and-sum beamforming method the cross-correlation image can be obtained by forming the detection beam in the direction given by the angle $\theta_m$ by summation of all sensor signals with corresponding time delays:

$$u(t, \theta_m) = \sum_{i=0}^{N-1} w_i \cdot B_i\left(t - \frac{x_i}{c_a}\sin\theta_m\right) \qquad (2)$$

where $w_i$ are apodization or shading coefficients, $x_i$ is the coordinate of the i-th sensor, $c_a$ is the speed of acoustic waves in the sample, and N is the total number of sensors in a transducer array. For the shading coefficient, one may employ one of the standard window functions used in correlation and spectral analyses, for example Hamming window, or a more sophisticated apodization function can be applied to minimize lateral sidelobes. In the case of near-field imaging, the delay time in equation (2) may also include a term quadratic with respect to $x_i$ to take into account the wavefront curvature, which can be essential for dynamic focusing of the phased array probe. The result of the processing for multiple angles $\theta_m$ is a set of m radial beams covering a sector of interest in the test sample.

In another embodiment, a frequency-domain method of image formation may be employed that takes advantage of the limited signal bandwidth and frequency-domain beamforming algorithm. This method does not require time-domain representations of cross-correlation functions $B_j(t)$ as in equation (2) but operates directly on the Fourier spectra $B_j(\omega)$ computed as a weighted product of $S_j(\omega)$ and $S_r^*(\omega)$:

$$B_j(\omega) = w_j S_r^*(\omega) S_j(\omega) \qquad (3)$$

where $w_j$—are the same apodization coefficients as in (2). Then the entire set of detection beams in Fourier domain can be represented by a matrix $U_{mk}$ with dimensions $N_b \times N_t$, where $N_b$ is the number of beams and $N_t$ the number of discrete frequency bins:

$$U_{mk} = \Sigma_{j=0}^{N-1} w_j B_j(\omega_k) \exp(-i\omega_k \tau_{jm}) \qquad (4)$$

where $\tau_{jm}$ is delay time applied to the j-th element for the m-th direction angle. Since the spectrum of the modulation chirp is limited to a finite bandwidth $f_1 < f < f_2$, the above operation can be applied only to the subset of frequencies $f_1 \cdot T_{ch} < k < f_2 \cdot T_{ch}$ instead of the entire signal spectrum with dimension $N_t$. The band-limited nature of received signals and frequency domain beamforming allow one to reduce computation time dramatically compared with the standard time domain delay-and-sum algorithm. Following computation of the matrix $U_{mk}$, the cross-correlation beams in time-domain for each angle $\theta_m$ can be obtained performing m inverse Fourier transforms:

$$u_m(t) = F_k^{-1}\{U_{mk}\} \qquad (5)$$

Finally, in step 240, the resulting correlation image may be displayed. This final step of image formation involves back-projection of the radial beam $u(r=c_a t, \theta)$ to the imaging plane and interpolation of the polar coordinate data to a Cartesian grid suitable for image display. This back projection step may involve bilinear interpolation of the polar mapped data (r, θ) to rectangular Cartesian grid and resulting sector image is displayed in a manner similar to conventional ultrasound. The signal processing described above may be performed off-line in post-acquisition mode, or in real-time. Real-time imaging may be achieved using simultaneous acquisition of parallel data channels and hardware implemented signal processing, as noted above.

In another embodiment, the photoacoustic imaging system may also include an ultrasonic source (for example, a High Intensity Focused Ultrasound (HIFU) transducer). In the example implementation involving the use of a HIFU, the HIFU is driven by a chirp waveform identical to the laser (optical) modulation chirp, but delayed in order to account for the differences between the speeds of light and sound. The HIFU radiates a region of interest (ROI) at the location of the laser light incidence at a phase shift with respect to the optical chirp which increases the generated photoacoustic signal (ultrasound-aided photoacoustics). The photoacoustic signal is enhanced through the HIFU-induced ultrasonic-force-mediated expansion of the target and stronger collapse following the acoustic rarefaction half-cycle of each chirp period. At the same time during the HIFU-induced acoustic compression half-cycle optical irradiation of the target with diminished volume generates a higher temperature which produces a stronger thermoelastic effect and stronger photoacoustic signal.

Figure 3:
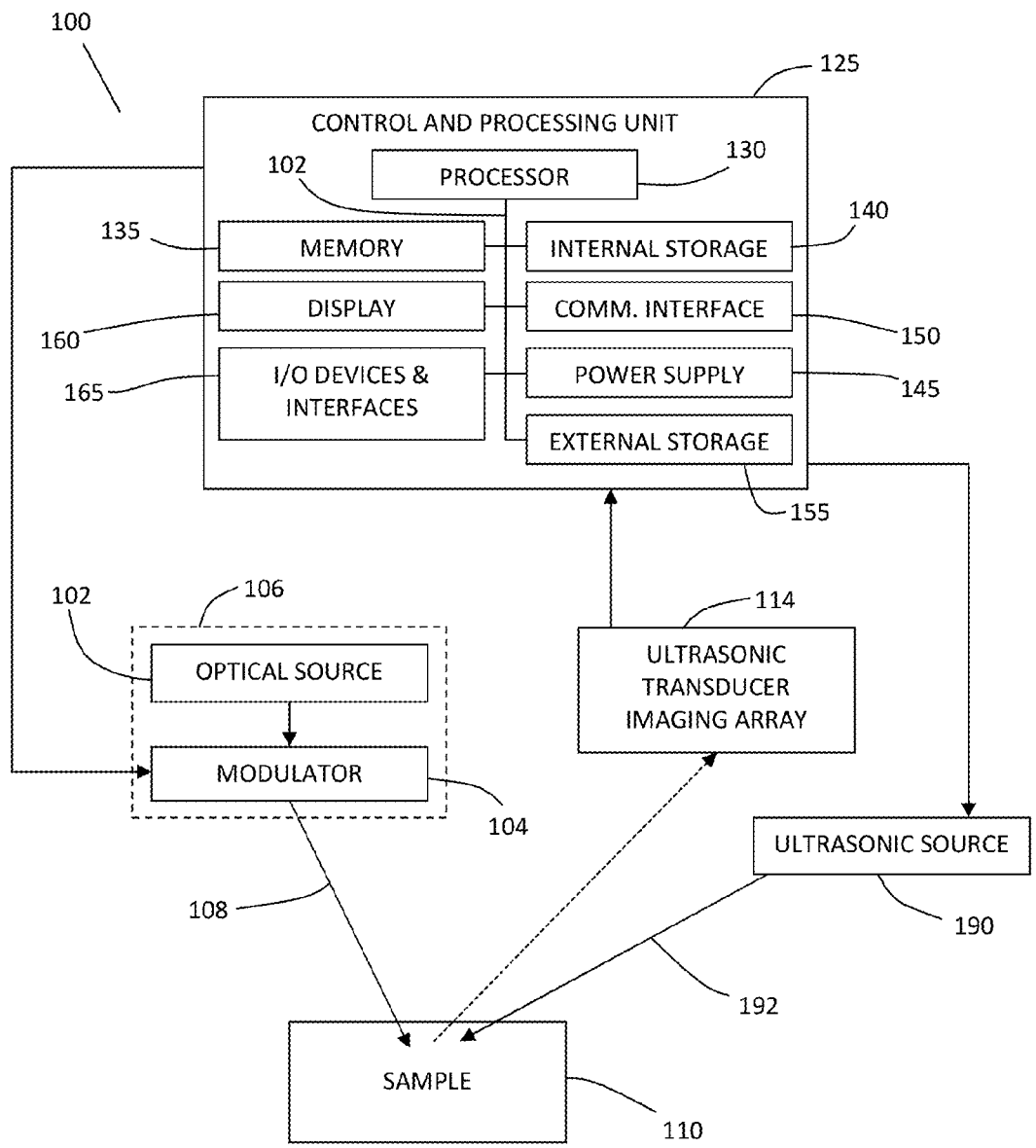
FIG. 3 illustrates an example of a system for performing photoacoustic imaging with a transducer array and correlation image post-processing and co-irradiating the beam with an additional ultrasonic beam.

In another HIFU embodiment, a focused HIFU is driven by a fixed frequency (fundamental or harmonic) and directed to the target thereby causing localized heating. Optical excitation using modulation frequency chirps and cross-correlation analysis as discussed above of the same region of interest (ROI) generates photoacoustic signals of enhanced magnitude due to the increased local temperature. FIG. 3 illustrates this alternative system embodiment including an ultrasonic source 190 (e.g. a HIFU) for locally heating with an ultrasound beam 192 the probed sample region of interest.

Depth-Resolved Photoacoustic Imaging with a Modulated CW Laser Source

Generation of photoacoustic response in a targeted sample occurs in the process of absorption and rapid thermalization of the absorbed optical energy leading to spatially non-uniform temperature distribution followed by thermoelastic deformations acting as the sources of acoustic waves. Since the magnitude of a photoacoustic source q is proportional to the first time-derivative of the temperature ($q \sim \partial T/\partial t$), the optical source must be modulated in time for efficient sound generation.

The simplest form of modulation consists of a single short laser pulse when a test specimen is exposed to intense laser beam within 5-10 ns time interval. Alternatively, as noted above, a CW optical source can be intensity modulated with high frequency using a modulation or chopping device, for example, an acousto-optic modulator, to interrupt the beam for short periods of time, thereby producing a periodic irradiation pattern.

Regardless of modulation implementation, the photoacoustic pressure P can be expressed using the Fourier transform of the wave equation given by:

$$\nabla^2 P(\vec{r}, \omega) + k^2 P(\vec{r}, \omega) = -\frac{i\omega\beta}{C_p} \tilde{q}(\vec{r}, \omega) \qquad (6)$$

where $k = \omega/c_a$ is the acoustic wave number, $c_a$ is the speed of acoustic waves in tissue, $C_p$ is the specific heat at constant pressure, β is the coefficient of thermal expansion, and q describes the spectrum of the spatially distributed photothermal sources.

The frequency domain description given by Eq. (6) is convenient because it allows one to abstract specifics of the modulation pattern and analyze the photoacoustic response for various experimental scenarios. To solve Eq. (6), the spatial distribution of the source function q and appropriate boundary conditions must be specified. The Transfer Function Method can be employed to relate the acoustic pressure spectrum P(ω) to the modulation waveform spectrum F(ω) in a way similar to theory of Linear Systems:

$$P(z, \omega) = I_0 \cdot H_{PA}(\omega) \cdot F(\omega) \cdot \exp(i\omega z/c_a) \qquad (7)$$

where $I_0$ is laser irradiance of the sample surface. In terms of signal analysis, Eq. (7) represents photoacoustic generation as a "filtering" process of the input signal f(t) by a linear system with the spectral transfer function $H_{PA}(\omega)$ while the laser irradiance $I_0$ is merely a scaling factor and $\exp(i\omega z/c_a)$ is the phase shift due to acoustic travel time delay $z/c_a$ to the receiving transducer.

Generally, the photoacoustic transfer function $H_{PA}(\omega)$ depends on the specific geometry, tissue optical and thermoelastic properties, as well as the boundary conditions. For example, a one-dimensional uniform absorbing layer with the absorption coefficient $\mu_a$ and the thickness L immersed in fluid environment with the acoustic impedance $\rho_f c_f$ is characterize by the transfer function:

$$H_{PA}(\omega) = \quad (8)$$

$$\frac{i\beta\mu_a c_s}{C_p(\mu_a^2 c_s^2 + \omega^2)} \cdot \frac{\left(\frac{\xi\omega}{c_f} + i\mu_a\right)F_1 - \left(\frac{\omega}{c_s} + i\xi\frac{\mu_a c_s}{c_f}\right)F_2 - 2\left(\xi\frac{\omega}{c_f} + i\mu_a\right)F_3}{\left(\frac{1}{c_s^2} + \frac{\xi^2}{c_f^2}\right)F_2 - \frac{2\xi}{c_s c_f}F_1}$$

where $$F_1 = e^{i(k_s - k_f)L} + e^{-i(k_s + k_f)L}, F_2 = e^{-i(k_s + k_f)L} - e^{i(k_s - k_f)L}, F_3 = e^{-(ik_f + \mu_a)L}$$

and $\xi = \rho_s c_s / \rho_f c_f$ is the acoustic impedance ratio of the solid layer and the coupling fluid, $k_s = w/c_s$ and $k_f = w/c_f$ are the corresponding wave number in the solid and the fluid.

Eq. (7) for the acoustic pressure spectrum with the transfer function given by Eq. (8) implies that the sample layer occupies one-dimensional space $0 \le z \le L$ and the acoustic wave propagates in the negative direction of the z-axis. In case of perfect acoustic matching of the layer to coupling fluid ($\rho_s c_s = \rho_f c_f$), Eq. (8) can be simplified significantly:

$$H_{PA}(\omega) = \frac{-i\beta\mu_a c_a^2}{2C_p} \cdot \frac{(\omega + i\mu_a c_a)}{(\mu_a^2 c_a^2 + \omega^2)}\left\{1 - \exp\left[-\left(\frac{i\omega}{c_a} + \mu_a\right)L\right]\right\} \quad (9)$$

Eqs. (4) and (5) demonstrate that the physics of the photoacoustic conversion is described entirely by the function $H_{PA}(\omega)$ regardless of the form of modulation of an optical source. Therefore, the main difference between pulsed photoacoustic modality and modulated CW technique is in the form of the function $F(\omega)$.

In case of a short laser pulse excitation with duration $t_L < 10$ ns, the excitation spectrum $F(\omega)$ is nearly constant over a very broad frequency range and the acoustic pressure spectrum is directly proportional to $H_{PA}(\omega)$. Therefore, the temporal profile of acoustic transients generated by short laser pulses is given by the layer impulse response and can be found using the inverse Fourier transform of the photoacoustic transfer function:

$$p(t) \sim I_0 \int_{-\infty}^{\infty} H_{PA}(\omega)F(\omega)\exp\left[i\omega\left(t + \frac{z}{c_a}\right)\right]d\omega \quad (10)$$

In case of harmonic modulation of a laser beam at the angular frequency $\omega_0$, the excitation spectrum can be considered as a Dirac delta-function $F(\omega) = 2\pi\delta(\omega - \omega_0)$. Such a modulated laser beam is expected to generate a narrow-band ultrasonic signal at the same angular frequency $\omega_0$.

Although photoacoustic generation and detection of narrow-band signals finds numerous applications in spectroscopic measurements, their use for spatially resolved imaging is limited due to two major factors: first, axial resolution of very narrow-band signals is extremely poor which makes them unsuitable for spatially resolved measurements, and second, the mean power of CW optical sources is typically several orders of magnitude lower than alternative pulsed systems, which results in very low SNR of the received signals.

Embodiments disclosed above address these two challenges by customizing optical excitation waveforms with finite bandwidth ("waveform engineering"; for example, chirped waveforms of particular shapes) and using correlation signal processing to increase SNR of each ultrasonic sensor in the transducer array.

Linear frequency modulated waveforms (chirps) with the bandwidth $\Delta f$ can provide maximum axial resolution $\Delta z = c_a / \Delta f$. For example, a typical chirped modulation waveform with the bandwidth $\Delta f = 4$ MHz theoretically provides axial resolution about 375 μm, which is sufficient for many imaging applications.

In contrast to pulsed photoacoustic excitation resulting in Eq. (10), information obtained with frequency domain correlation methods is quite different. It can be shown using Eq. (1) with $S_r(\omega) \equiv F(\omega)$ and $S_t(\omega) \equiv W(\omega) \cdot P(\omega)$, where $W(\omega)$ is a spectral windowing function representing ultrasonic transducer spectral sensitivity. Using Eq. (7), the Fourier spectrum of the correlation function can be written as:

$$B(\omega) = I_0 W(\omega) \cdot H(\omega) \cdot |F(\omega)|^2 \exp\left(\frac{i\omega z}{c_a}\right) \quad (11)$$

while the temporal profile can be obtained by the inverse Fourier transform of Eq. (11):

$$B(t) = \frac{I_0}{2\pi}\int_{-\infty}^{\infty} W(\omega)H(\omega)|F(\omega)|^2 \exp\left[i\omega\left(t + \frac{z}{c_a}\right)\right]d\omega \quad (12)$$

The analytical solution of the integral in Eq. (12) is difficult mathematically even for the simplified transfer function given by Eq. (9), but can be computed numerically using Eq. (8) for $H_{PA}(\omega)$ and the Fourier transform of the specific modulation function $F(\omega)$.

Figure 4:
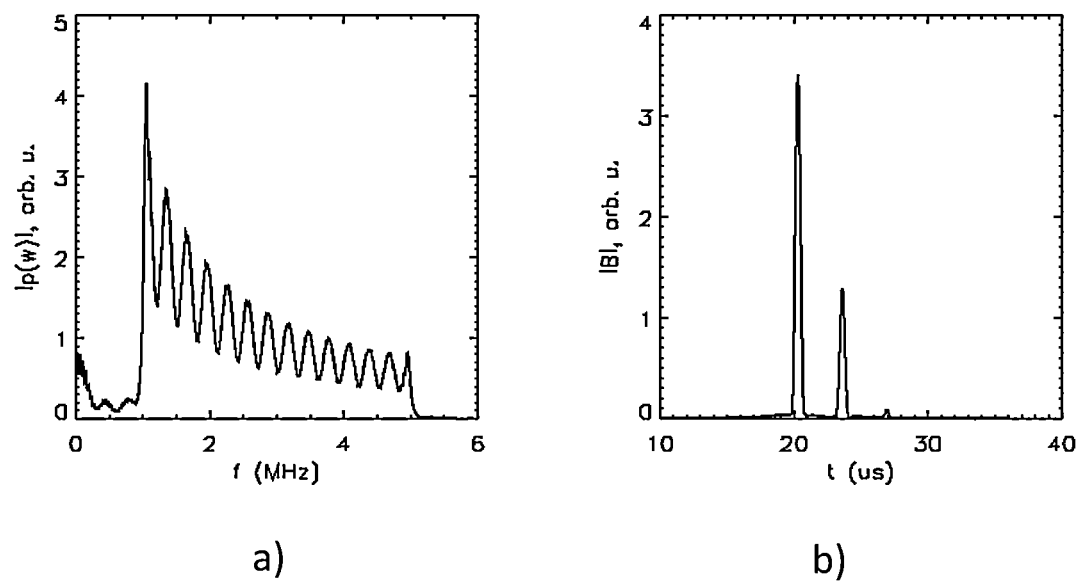
FIG. 4 plots (a) the spectrum of the photoacoustic pressure and (b) the correlation function B(t) as computed numerically using computation for a uniform absorbing layer with L=0.5 cm and $\mu_a=2$ cm$^{-1}$ positioned at the distance of |z|=3 cm.

The result of numerical computation for a uniform absorbing layer with $L = 0.5$ cm and $\mu_a = 2$ cm$^{-1}$ positioned at the distance of $|z| = 3$ cm is shown in FIG. 4. In agreement with Eqs. (4) and (9), the spectrum of the photoacoustic pressure (shown in FIG. 4(*a*)) is a replica of the chirp spectrum weighted by the transfer function $H_{PA}(\omega)$ while the correlation function B(t) (shown in FIG. 4(*b*)) peaks at the times $t = |z|/c_a$ indicating the spatial positions of photoacoustic sources. The second peak in FIG. 4*b* corresponds to movements of the back surface of the layer with the peak magnitude scaled down due to light attenuation in the layer. The double peak structure is explained by the band-limited nature of the irradiation chirps and the full width at half maximum of the peaks is equal to the reciprocal of the chirp bandwidth, i.e. ~250 ns. According to Eqs. (8) and (12), the magnitude of the correlation peaks is proportional to the product $\mu_a I_0$ which has the dimensions of W/cm$^3$ and corresponds to the absorbed optical energy per unit volume and unit time.

In summary, the foregoing discussion demonstrates that correlation processing of photoacoustic signals generated by a modulated CW optical source provides imaging information related to the spatial position of photoacoustic sources and the optical properties ($\mu_a$) of test samples.

Laser Sources for Frequency Domain Correlation Imaging

One implementation of the frequency domain photoacoustic technique and apparatus described above and shown in FIG. 1 can be realized with a laser source that can be modulated in the megahertz range and which delivers sufficient optical power of the near-IR radiation over a relatively large beam spot diameter (>1 cm). Additionally, for use in clinical applications, it would be beneficial for such a laser source to be portable to satisfy typical space constraints encountered in clinical applications and to enable integration with existing instruments such as ultrasound scanners.

A possible candidate that can meet the conditions of the above example is a high-power laser diode with modulated output controlled by electrical current. Use of electronically driven modulation can greatly simplify the generation of optical excitation with complex wave patterns, for example, non-linear chirps, phase modulated and coded waveforms (e.g. Golay, Barker etc.), where such waveforms are engineered to ensure sufficiently high frequency-domain photoacoustic SNR.

An additional important feature of optical sources configured and provided using laser diodes is the convenience of laser beam delivery to a targeted sample by means of optical fibers attached directly to the diode head. The laser beam emerging from the fiber tip can be shaped to deliver a desired illumination pattern using collimators, cylindrical lenses and other custom optical elements. In order to increase the optical irradiance incident on the sample surface, several laser diodes can be synchronized by a single driving signal waveform and the outputs of multiple diode heads can be merged together in a single optical fiber or a bundle of fibers.

Customized Optical Waveform Design for Frequency Domain Photoacoustic Radar Imaging Laser Safety and Improved SNR Eq. (12) shows that the correlation signal is proportional to the laser irradiance $I_0$ and SNR can be increased by increasing the mean power of CW optical source. This simple way to increase SNR has limited utility in clinical settings due to safety regulations imposed to prevent irreversible damage that may be caused by laser radiation. Therefore, the optical power used to irradiate tissue sample must conform to the Maximum Permissible Exposure (MPE) level.

Figure 5:
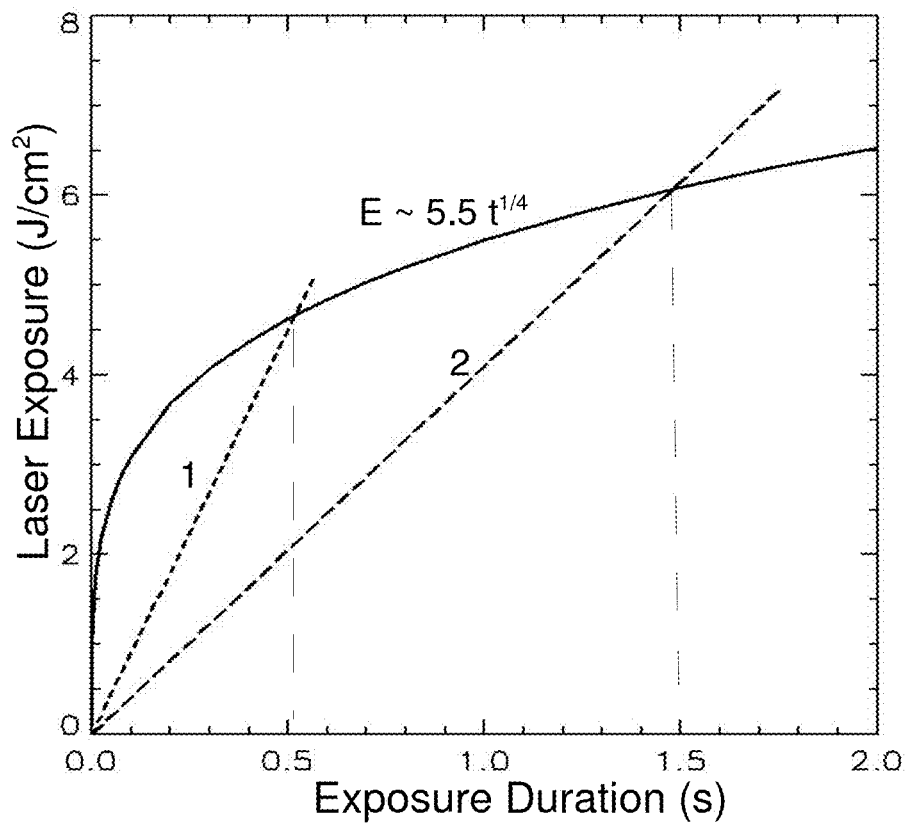
FIG. 5 plots the maximum permissible exposure (MPE) as a function of exposure duration t through the following equation: EMPE=$5.5t^{0.25}$ [J/cm$^2$].

The safety standard sets MPE as a function of exposure duration t through the following equation: $E_{MPE}=5.5t^{0.25}$ [J/cm$^2$], valid for the wavelength range $\lambda$=400-1400 nm and for times t in the range $10^{-7}$–10 s. Graphically, the safety curve is shown in FIG. 5 (solid line). The area below the solid line is the safety zone for various exposure times. The laser exposure E produced by a laser with irradiance $I_0$ and chirp duration $T_{ch}$ is $E=I_0 \cdot T_{ch}$ which is a linear function of time $T_{ch}$ for the constant $I_0$. Two examples of laser irradiance with $I_0$=9 W/cm$^2$ and 4 W/cm$^2$ are shown as dashed lines in FIG. 5 that intersect the safety curve, respectively at times $$t_{max} = \left(\frac{5.5}{I_0}\right)^{4/3} = 0.5 \text{ s and } 1.5 \text{ s}. \tag{13}$$

Therefore, to optimize the SNR of the frequency domain photoacoustic method, a combination of the three parameters: laser irradiance $I_0$, exposure duration $T_{ch}$ and $E_{MPE}$ must be considered.

The strong nonlinearity of the MPE curve versus exposure time carries an important implication for the SNR and the trade-off between laser power and chirp duration. The standard expression for correlation processing SNR under the constraints of the MPE can be written as:

$$SNR_{MF} = \frac{2E_s}{N_0} = \frac{A^2 T_{ch}}{N_0} \tag{14}$$

where $E_s$ is the signal energy, A is the signal amplitude, $T_{ch}$ is the chirp duration and $N_0$ is the white noise power spectral density. It follows from Eq. (14) that both large signal amplitude $A\sim I_0$ and long chirp duration $T_{ch}$ improve SNR. However, the laser irradiance $I_0$ must be related to $T_{ch}$ according to the safety standard set by $E_{MPE}$. Taking into account the safety curve and Eq. (14), it is easy to show that for two laser chirps with $I_{01}$ and $I_{02}$ at the safety limit and corresponding durations $T_{ch1}$ and $T_{ch2}$, the ratio of the two SNRs is:

$$\frac{SNR_2}{SNR_1} = \left(\frac{T_{ch1}}{T_{ch2}}\right)^{1/2} \tag{15}$$

Equation (15) shows that $SNR_2 > SNR_1$ if $T_{ch2} < T_{ch1}$.

This result is an important result for optical waveform engineering design of laser sources intended for frequency-domain photoacoustic imaging as it shows that SNR of correlation processing can be increased by simultaneously shrinking exposure time and increasing A (or $I_0$) without violating safety regulations. Thus, for the two examples depicted in FIG. 5, the one with irradiance 9 W/cm$^2$ and $T_{ch}$=0.5 s (FIG. 5, straight line 1), is expected to have higher SNR than the one with $I_0$=4 W/cm$^2$ and $T_{ch}$=1.5 s (FIG. 5, line 2).

Accordingly, since the power of CW lasers is always limited, a simple prescription for maximizing SNR can be formulated as follows: the maximum available surface irradiance is set and the chirp duration is subsequently adjusted according to the safety curve.

In summary, Equation 14 points to potentially significant SNR improvement by using short, high irradiance (or peak power) optical pulse chirps, a fact that was tested and demonstrated experimentally by the inventors using acousto-optic sine-wave chirp modulation.

The aforementioned analysis and experimental support led the inventors to conclude that optimal laser source waveform design for a multi-channel photoacoustic radar imager does not consist of compact near-IR laser CW laser diodes driven by sine-wave chirps, as conventionally done with ultrasonic and other radar schemes. Instead, the inventors realized that the signal to noise for a multi-channel photoacoustic radar imager can be improved with waveform engineering by varying the modulation pattern, laser irradiance and exposure so as to maximize the $A^2 T_{ch}$ product under MPE restrictions.

Accordingly, in one example implementation, a suitable laser source for use multi-channel photoacoustic radar imaging consists of a set of laser diodes modulated in-sync by the electrical current to produce sufficient optical power (for example, exceeding 10 W) and modulation frequencies in the range of approximately 1-5 MHz (or higher, such as approximately 1-25 MHz). The full-chirp repetition rate exhibited by available specialty semiconductor laser diodes is in approximately the 1-2 kHz range, and may be extended to approximately the 1-10 kHz range.

Although conventional pulsed-laser photoacoustic systems provide valuable optical contrast information, the low repetition rate (~10-20 Hz) of today's nanosecond pulsed lasers can be notoriously slow even in the presence of multi-transducer detection arrays. The slow pulse repetition rate of Q-switched lasers restricts imaging to the 20-30 sec/image range. This problem is especially severe for three-dimensional photoacoustic imaging of large tissue areas such as the female breast. Given the large number of pulses required for full-frame image acquisition, the slow repetition rates seriously limit image formation, a true impediment to real-time applications.

In contrast, with the aforementioned modulated laser source design of selected embodiments of the disclosure, the photoacoustic radar imager can speed up the image acquisition process close to 5-10 images/sec, well beyond the 20-30 sec/image typical of ns pulsed laser repetition rates. This is a major step toward developing a portable imaging instrument suitable for clinical use. While commercial high-repetition-rate pulsed lasers (1 kHz) can deliver 8 images/sec performance, the maximum permitted exposure laser safety standard is exceeded and portability is sacrificed. The relatively poor noise performance of high-repetition-rate pulsed lasers due to jitter and inefficient high-pass filtering in the presence of strong optical scattering exhibited by soft tissues limits penetration depth up to 1 mm [Maslov K, Zhang H F, Hu S, Wang L V. *Optical-resolution photoacoustic microscopy for in vivo imaging of single capillary*. Opt Lett 2008; 33: 929-32; Allen T J, Alam S, Zhang E Z, Laufer J G, Richardson D J, Beard PC. *Use of a pulsed fibre laser as an excitation source for photoacoustic tomography*. Proc SPIE 2011; 7899: 78991V], thereby making it difficult or impossible to generate depth resolved PA tomographic imaging. On the contrary, the efficient noise-filtering action of cross-correlation frequency-domain photoacoustic radar with pulse compression can deliver higher frame rates without too much noise penalty and without exceeding the MPE standard due to the limited and adjustable chirp bandwidth.

High-irradiance and high-frequency pulsed chirps are very compatible with commercial ultrasonic imager burst repetition rates. This renders potential integration of the present system into commercial biomedical ultrasonic imagers much simpler and straightforward than other photoacoustic imaging schemes using pulsed laser excitation.

Until recently, near-infrared (700-900 nm) semiconductor laser diodes operating under a broad range of externally driven chirped waveforms from sine-wave to square-wave to chirped pulses of adjustable duty cycle have not been available. However, such sources are now available from Laser Light Solutions, Princeton, N.J., and from OmniPulse Technology, San Diego, Calif. Laser Light Solutions have developed and constructed the first ever 808-nm diode laser system suitable for the presently disclosed frequency-domain photoacoustic radar imaging based on the foregoing waveform and emission parameter design. OmniPulse Technology can provide 1-25 MHz modulated chirped laser diodes and drivers for the purposes of deep and high-resolution photoacoustic radar tissue imaging.

In one embodiment that is useful for the measurement of vascular tissue, the aforementioned laser system may be modified to include a second wavelength in the form of a dual-wavelength laser source, which may be integrated within or with the photoacoustic hardware. The second wavelength is particularly useful in measuring the ratio of differential photoacoustic responses due to hemoglobin absorption: the different absorption coefficients of oxy- and deoxy-hemoglobin in blood aggregates can be an indicator of the presence of malignant or benign tumors. Such an embodiment is described in further detail below.

To summarize the preceding discussion, frequency-domain correlation photoacoustic imaging is capable of providing spatially resolved information on optical heterogeneities in the test samples through the correlation image recorded by a phased array of ultrasonic transducers. The magnitude of the correlation contrast in the photoacoustic images is proportional to the absorbed optical energy which yields information on optical properties and chemical composition of the imaging area. Possible applications where this technique can be used include, but are not confined to: imaging of the vascular network of tissue samples and measurements of hemoglobin oxygenation in the area of interest; endoscopic (esophageal and colon) diagnostics of the presence of blood, fatty tissue (plaque) and polyps; and deep seated tumors such as in breast tissue during the various stage of angiogenesis. Sensitivity of photoacoustic imaging to optical contrast and combined ultrasound-photoacoustic co-registration may improve breast cancer detection rate especially in patients with high-density breasts.

Modulation Waveform Engineering for Frequency-Domain Correlation Photoacoustic Imaging As noted above, an advantage and flexibility of the disclosed embodiments is their ability to customize photoacoustic responses by selecting appropriate waveforms for modulation of the optical source. Thus, the emitted CW optical radiation is coded by a specific function of time to optimize SNR and improve contrast and axial resolution of the resulting images. One example of the abovementioned coded waveforms that can be utilized to increase SNR and restore axial resolution on a scale less than 1 mm is a linear frequency-swept (chirp) modulation pattern. Other examples of intensity modulation include non-linear frequency sweeps.

Non-linear frequency modulation chirps can be generated through appropriate optical waveform engineering. The motivation for these waveforms is the possibility of benefiting from the maximum available bandwidth while concentrating more on the optimal or improved frequency range. For instance, if the chirp Power Spectral Density (PSD) mimics the photoacoustic response PSD, the cross-correlation generates the maximum spectral energy and therefore the highest peak. One proposed chirp family is:

$$r(t) = A_I \cos\left(\omega_c t + \frac{2\pi B}{nT_{ch}^{n-1}} t^n\right) \quad (16)$$

where the parameter n=2 for linear chirps and >2 for nonlinear chirps. It has been demonstrated that nonlinear chirps can increase the generated photoacoustic energy (magnitude of cross-correlation amplitude). However, these chirps also generate larger sidelobes and broaden the peak of the envelope correlation, thereby degrading axial resolution.

Figure 6:
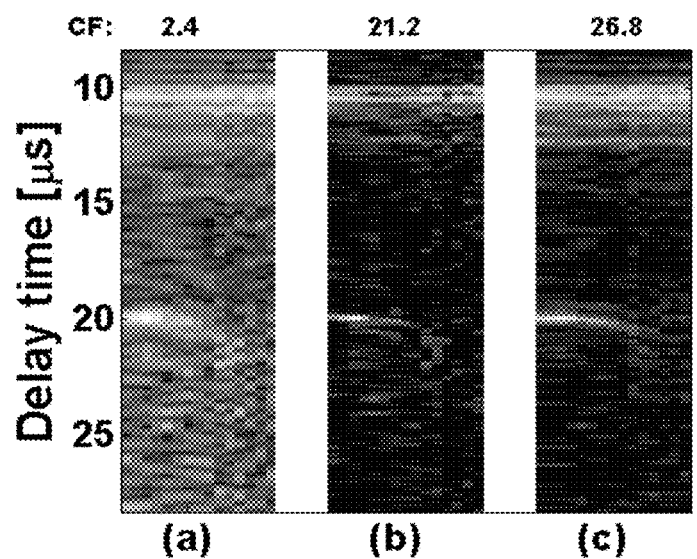
FIG. 6 shows photoacoustic images generated by (a) amplitude signal (linear chirp), (b) amplitude signal filtered by phase signal (linear chirp), (c) amplitude signal filtered by phase signal (nonlinear chirp), while (d) illustrates the position of the sample and a transducer of appropriate (MHz) frequency response as required from depth, axial and spatial resolution considerations of a given imaging object
Figure 6:
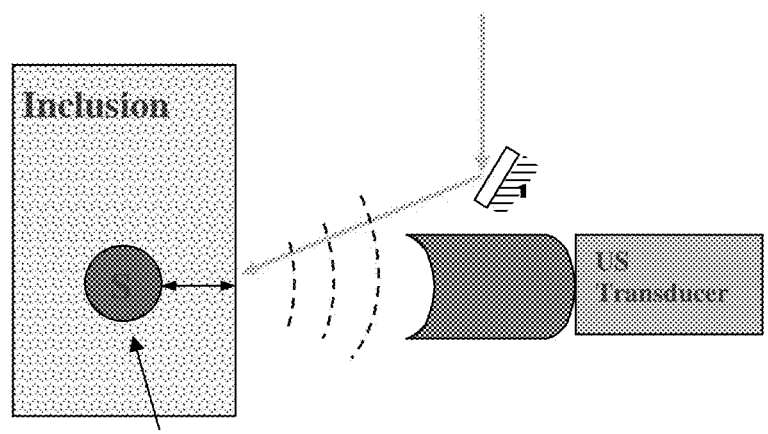

The nonlinear chirp SNR improvement property in the phase signal can be combined with a linear chirp amplitude signal to enhance the contrast and axial resolution of the combined image. FIG. 6 compares three images of a 6.4-mm diameter cylindrical inclusion located ~14 mm below the surface perpendicular to the plane of the image. FIG. 6(a) is the image generated by correlation amplitude with linear chirp (0.5-3 MHz bandwidth).

FIGS. 6(b) and (c) depict the amplitude image multiplied by linear and nonlinear phase signals, respectively. A broadened line and part of a curvature are visible in the images which are, respectively, related to the top surface of the phantom and the cylindrical inclusion. Since the inclusion was located very deep inside the medium, a linear time gain correction (TGC) was applied to the signals or the phantom surface signal would dwarf the inclusion signal. In all images, due to TGC, more speckle noise is observable below the inclusion than above it. To compare the contrast of the images, we use the following contrast measure suggested by Patterson and Foster:

$$CF = \frac{\text{Signal mean in the lesion} - \text{Signal mean in the background}}{\text{Signal mean in the background}} \quad (17)$$

The evaluated contrast factors (CF) were 2.4, 21.2 and 26.8 for images a, b and c, respectively. This shows that by using the phase signal obtained from a nonlinear chirp, the amplitude contrast and axial image resolution. FIG. 6(b)) can be enhanced more than 10 times. This is 26% higher than the amplitude image filtered by the phase image obtained with a linear chirp. Nonlinear amplitude-phase combination imaging algorithms can be readily added to array transducer photoacoustic imaging. Here only the transmitted signal will change to the designed nonlinear signal and amplitude/phase signals will be extracted as before. These signals can be combined for each element separately. Afterwards using the described phase array algorithm, the 2D image is produced for the assigned delay between the array elements so as to improve SNR for deep subsurface absorbers such as cancerous lesions in a human breast.

Another form of coded optical excitation may include phase manipulated waveforms (for example, Barker and Golay codes) to decrease sidelobes without spectral weighting which, in turn, may improve SNR and image contrast.

Imaging with coded waveforms offers improved performance relative to conventional ultrasound, and can yield an increase in SNR and imaging depth. The finite time required for transmit-receive cycles and dynamic focusing, as required by known imaging methods, places restrictions on the duration of ultrasonic pulses. In contrast, in some embodiments, photoacoustic imaging operates exclusively in reception mode, thus allowing the generation of much longer (>1 ms) signals and higher SNR gains.

The aforementioned phased array photoacoustic imaging embodiments may be employed for various biomedical applications such as noninvasive imaging of human vasculature and imaging of optical contrast related to tissue abnormalities. In one embodiment, the system may employ a standard ultrasonic array probe integrated with conventional ultrasound instrumentation for high-speed and interleaved image co-registration of tissues. The following section discusses the adaptation of photoacoustic radar imaging and ultrasonic image co-registration in greater detail.

Ultrasound and Photoacoustic Image Co-Registration

The use of ultrasonic transducer arrays for photoacoustic imaging allows one to combine two modalities (conventional ultrasound and frequency-domain photoacoustic) in one instrument capable of dual-mode imaging of the same tissue sample. Photoacoustic imaging provides excellent sensitivity to optical contrast but lacks information regarding internal anatomical structure and delineation of various tissue types. On the other hand, conventional ultrasound imaging provides high-resolution structural information related to discontinuities of mechanical properties but is not sensitive to the changes of chemical composition and early stage pathologies.

Combination of two imaging modalities in a single instrument and hybrid image co-registration may enhance diagnostic capability of each technique used separately. Therefore merits of ultrasound imaging, such as the delineation of a cancerous tumor boundaries, can be enhanced by optical contrast information delivered by the photoacoustic technique. One benefit of such interleaved photoacoustic and ultrasound (photoacoustic-ultrasound) co-registration of the physically different contrast mechanisms is the increased information content that may improve diagnostic power of conventional ultrasound. Another advantage of using photoacoustic radar technology for dual-mode imaging is the availability of ultrasound instrumentation that can be adapted for PA imaging. Combining the high repetition rate of laser chirps with the high-speed parallel data acquisition hardware, both imaging modalities can deliver real-time performance which is very important for clinical applications.

To enable dual-mode photoacoustic-ultrasound imaging, a standard ultrasound probe must be outfitted with an optical delivery system providing laser irradiation of the tissue surface. This can be accomplished by means of an optical fiber connecting a laser source and terminated by a single or several lens collimators that can be used for shaping the spatial illumination pattern.

In one embodiment, such a dual-mode imaging capability can be implemented as an add-on feature to existing clinical ultrasound instrumentation. In such a case, two specific design issues should be addressed. First, since laser illumination should coincide with the ultrasound imaging plane and cover the depth range from several millimeters to several centimeters, laser spot dimensions should closely match the aperture of the ultrasonic array and illuminate the area directly under the array.

Figure 7:
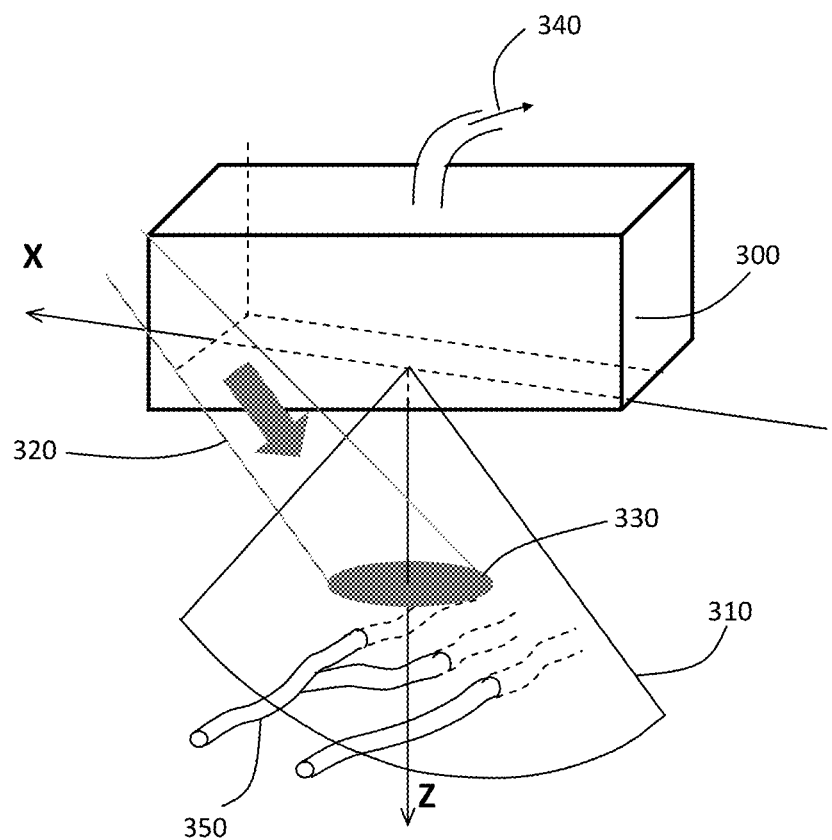
FIG. 7 shows a schematic of a frequency-domain photoacoustic imager.

Accordingly, in one embodiment, a layer of near-IR transparent ultrasonic coupling media (water or gel), with a suitable thickness (for example, about 1-2 cm) is inserted between the ultrasound probe and the tissue sample (for example, as shown in FIG. 7).

In embodiments in which the laser irradiation is not expected to be on all the time, suitable means may be provided to enable the initiation of laser irradiation and interruption of normal ultrasonic operation, in order to initiate collection of the photoacoustic data. This can be accomplished according to a wide variety of implementations, such as a push button or a foot switch that triggers the laser source and changes the ultrasonic array into reception mode. After a specific time of laser exposure, normal ultrasound imaging operation may be resumed, for example, while the system software provides data processing and image display.

Figure 11:
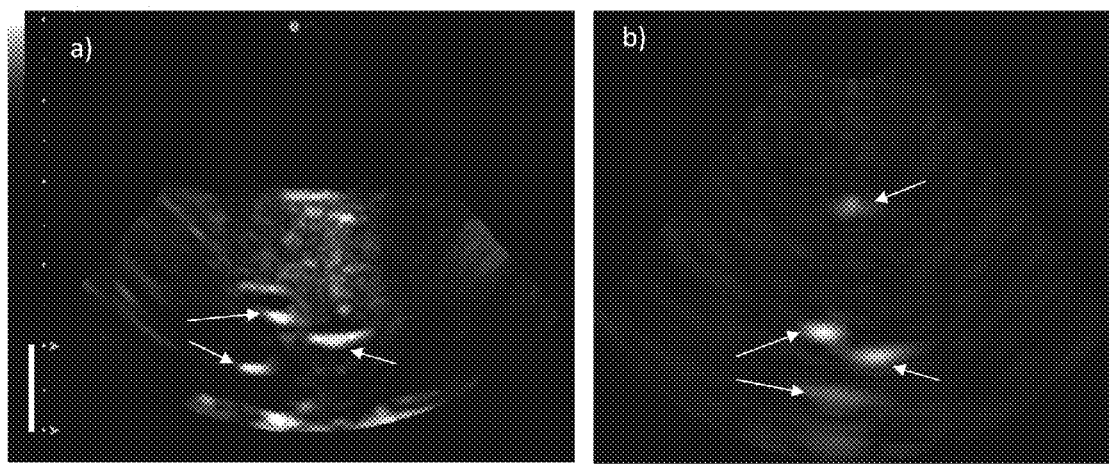
FIG. 11 shows (a) shows an example of dual-mode (ultrasound (a) and photoacoustic (b)) imaging of the same tissue specimen (chicken breast) with artificially embedded optical contrast (three wires, 200 um in diameter). Wires are labeled by the arrows and the scale bar is 1 cm.

Accordingly, alternating photoacoustic-ultrasound and ultrasound imaging can be repeated, for example, at the operator's request or according to a pre-selected and/or automated protocol, and the resulting images can be displayed. In some embodiments, the images may be presented separately, such as side-by-side (for example, as shown in FIG. 11) on a split-screen monitor. In other embodiments, the images may be fused together in a single image. Color coding may be employed to show different contributions to the single images from the two different imaging modalities.

An example of dual-mode imaging of a tissue sample ex-vivo with artificial optical heterogeneities using a standard clinical ultrasonic scanner and photoacoustic radar sharing the same phased array probe is shown in FIG. 11, as described further below.

Wavelength-Modulated Differential Spectroscopic Photoacoustic Radar

Although the current state of the art of the photoacoustic radar when compared to conventional pulsed laser photoacoustic imaging systems yields theoretical estimates of SNR advantage of the latter on the order of 10 dB [Telenkov and Mandelis (2011)], experimental results show a much smaller SNR difference due to 1) the limited frequency-domain ability to tune the laser irradiation modulation frequency spectrum within the transducer optimal bandwidth; and 2) the inability to efficiently suppress the signal baseline of pulsed laser systems even after high-pass filtering.

Nevertheless, the effective similar SNRs can be tilted in favor of the photoacoustic radar through improvements in terms of contrast and resolution. The latter can render the performance and tumor specificity of the photoacoustic radar imager superior to that of pulsed photoacoustic imagers, and utilizing the availability of compact and inexpensive CW laser diodes with a wide wavelength selection in comparison with bulky and expensive Q-switched pulsed lasers. This opens the possibility for more sensitive photoacoustic imagers than today's state-of-the-art either as stand-alone photoacoustic instruments or in co-registration with commercial clinical ultrasound imagers.

Conventionally, the contrast of biomedical photoacoustic imaging systems is generated by absorption coefficient differences in the presence of blood in the 650-1000 nm spectral range in cancerous tissue compared to blood-poor healthy tissue. The photoacoustic contrast increases proportionally to the concentration of blood (angiogenesis), i.e. linearly with the (different) optical absorption coefficients $\mu_{a,Hb}$, $\mu_{a,HbO2}$, of hemoglobin (or de-oxyhemoglobin, Hb) and oxyhemoglobin (HbO$_2$), respectively, of the interrogated tissue region of interest (ROI) at the excitation wavelength. This absorption coefficient distinction is very important, because while angiogenesis can increase Hb concentration, tumor hypermetabolism can decrease oxygen saturated hemoglobin HbO$_2$. This effect is, along with angiogenesis, the hallmark of cancer, and one should be able to clearly measure the two concentrations in order to identify the presence of cancer using the absorption coefficients at two wavelengths:

$$\mu_a(\lambda_1) = \ln(10)\epsilon_{ox}(\lambda_1)C_{ox} + \ln(10)\epsilon_{de}(\lambda_1)C_{de} \quad (18)$$

$$\mu_a(\lambda_2) = \ln(10)\epsilon_{ox}(\lambda_2)C_{ox} + \ln(10)\epsilon_{de}(\lambda_2)C_{de} \quad (19)$$

In these equations, $\lambda_1$, $\lambda_2$ are the two wavelengths, $\epsilon_{ox}$ and $\epsilon_{de}$ are the known molar extinction coefficients of oxy- and de-oxyhemoglobin, respectively, and $C_{ox}$, $C_{de}$ are the molar concentrations of oxy- and de-oxyhemoglobin, respectively, in the optically interrogated tissue.

However, with pulsed laser excitation, background absorptions as well as ultrasonic transducer reverberations ("ringing") [Telenkov and Mandelis (2010)] tend to compromise the specificity and sensitivity of photoacoustic contrast to a rather high detection threshold of the lowest possible accumulation of angiogenetic oxygen-poor hemoglobin in malignant (cancerous) lesions such as those encountered in human breast imaging.

Figure 12:
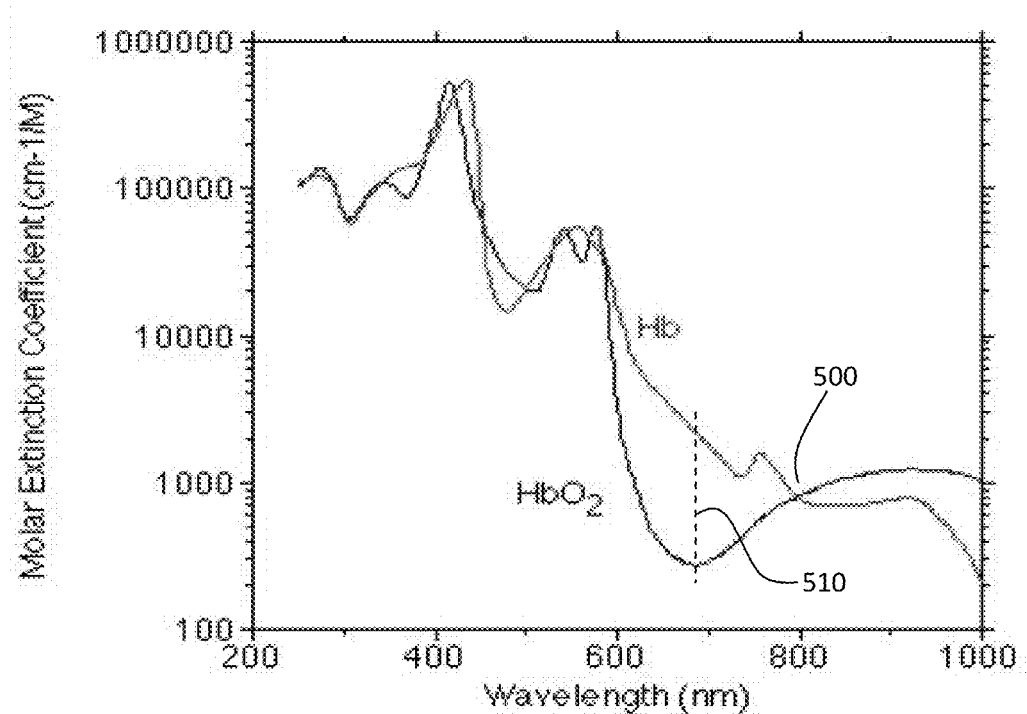
FIG. 12 plots the hemoglobin and oxy-hemoglobin absorption spectrum with the isosbestic point shown at ca. 780 nm.

The use of a spectral reference where the absorption coefficients of both HbO$_2$ and oxygen-poor (Hb) hemoglobin are equal (the isosbestic point 500, ca. 780-800 nm), as shown in FIG. 12, is important as it can yield higher or lower signals when compared with absorptions in the e.g. 680 nm range (shown at 510) where the Hb absorption coefficient is higher than at the isosbestic point 500, while that of HbO$_2$ is lower. If this is done sequentially as differential imaging, it will improve somewhat the dynamic range of the measurement through image normalization at two wavelengths, but the spatial overlap matching of features from adjacent absorbers is imperfect and the post-processing ratioing errors limit the inherent spectroscopic capabilities of the technique, also compromising its ability to identify higher and lower absorptions/signals at the non-reference wavelength. To the best knowledge of the inventors, blood concentration measurements have only been made in arterial and veinous configurations using longer wavelength lasers (e.g. 905 nm [Saerchen et al (2011)]) with single-point total hemoglobin concentration ($C_{Hb} = C_{ox} + C_{de}$) measurements limited in the 4-16 g/dL range. There appear to be no data on $C_{Hb}$ detection limits in tissues and/or using photoacoustic imaging.

The aforementioned embodiments of the frequency domain (e.g. chirped) photoacoustic radar, gives rise to the unique possibility of implementing, in contrast to the differential scheme of the preceding paragraph, a truly differential spectroscopic system and method using the cross-correlation method disclosed above to monitor minute differences in absorption coefficients by using two optical souces (such as semiconductor laser diodes) operating at the different wavelengths.

For example, in one embodiment, one optical source possibly emitting in the 680 nm range where there exists a local maximum difference in absorption coefficients between HbO$_2$ and Hb for optimum discrimination between the two types of blood, and the other diode emitting at, or close to, the isosbestic point (~780 nm).

Figure 14:
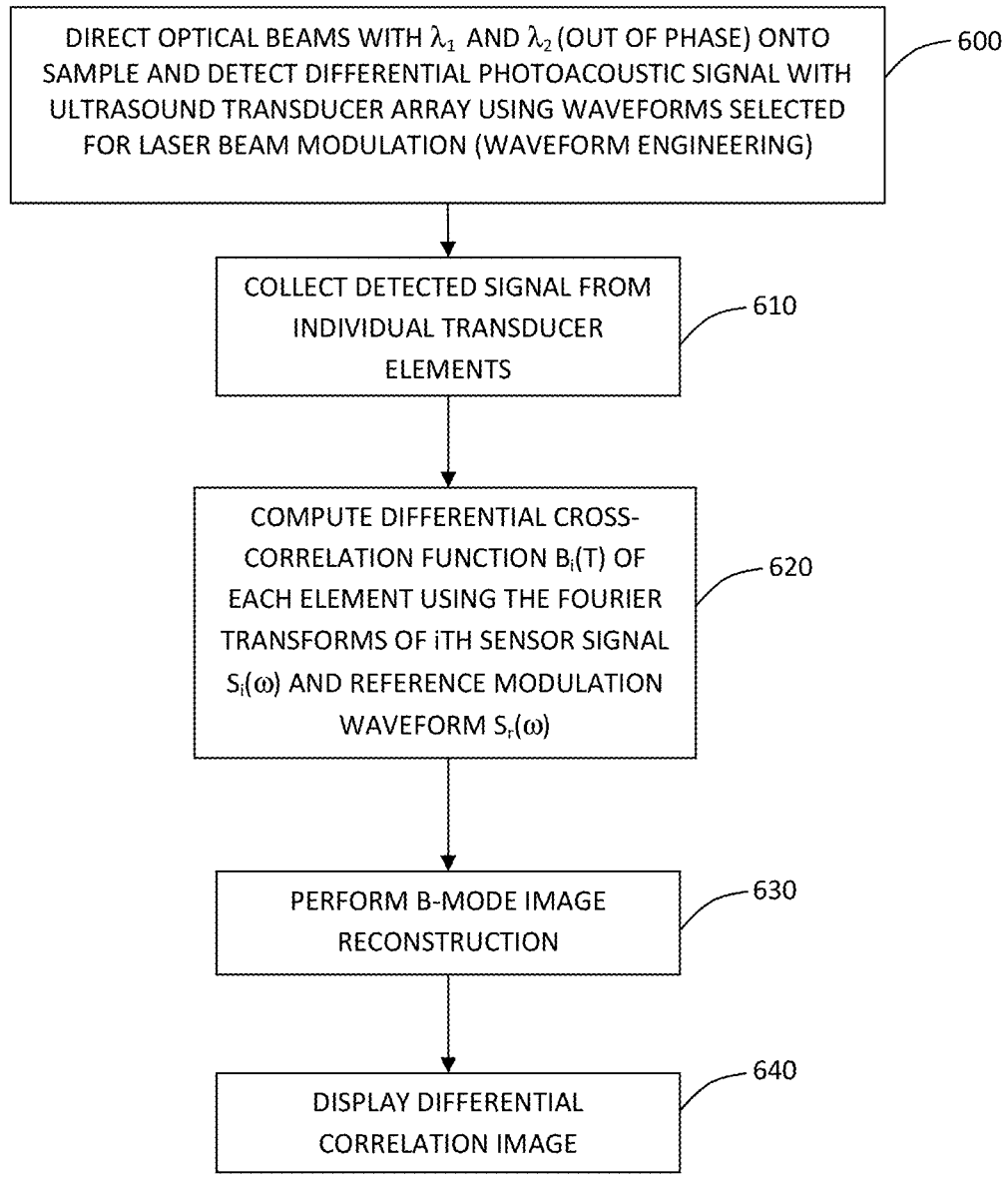
FIG. 14 is a flow chart describing a differential wavelength method of performing array-based photoacoustic imaging.

Such a differential spectroscopic photoacoustic radar system may be employed by launching two out-of-phase chirp-modulation waveforms (e.g. waveforms differing in phase by approximately 180 degrees), each modulating the current of each laser, with the two beams focused on the same spot of a tissue sample (or a blood-containing phantom, for example, during testing or calibration), as shown in step 600 of the flow chart shown in FIG. 14. The remainder of the processing steps of the method are similar to those outlined in FIG. 2, where the reference waveform used in calculating the cross-correlation image is modulating at the isosbestic wavelength.

The system could be calibrated so as to emit approximately the same number of photons at both wavelengths, given that the absorption coefficient of blood is dependent linearly on the hemoglobin concentration: $\mu_a(\text{blood}) = \epsilon(\text{blood})[C_{Hb}]$, where $\epsilon$ is the extinction coefficient and [ ] indicates concentration. Owing to the approximate 180 degree phase shift between the two modulation chirps, the output is a differential photoacoustic signal, in which the maximum pressure wave compression at one wavelength will be counterbalanced by the maximum rarefaction at the other.

Accordingly, the photoacoustic signal is directly proportional to the difference in absorption coefficients between the isosbestic and the additional spectral point at the same spatial location in real time, thereby yielding a sensitive contrast image. This image can be directly interpreted in terms of oxygenated (negative peak in cross-correlation subtraction, or negative phase if single frequency out-of-phase wavelength modulation is used coupled to lock-in amplifier demodulation) or non-oxygenated (positive peak or positive phase) of blood concentration, in the interrogated tissue.

The system could be tested and/or calibrated with several concentrations of both HbO$_2$ and Hb, in order to construct curves of photoacoustic cross-correlation peak threshold and full amplitude ranges vs. HbO$_2$ and Hb absorptions (i.e. concentrations). The magnitude of the cross-correlation and/or the phase difference under single-frequency lock-in detection can be calibrated to measure the degree of oxygenation of blood hemoglobin at or near 680 nm.

The differential spectroscopic cross-correlation photoacoustic imaging systems and methods described herein cannot be achieved using pulsed laser photoacoustic detection, even if two wavelengths can be implemented sequentially, because differences between two large incoherent photoacoustic signals and the concomitant noise levels cannot subtract as efficiently as two coherent signals, both of which enter into the same (simultaneous) or sequential (one wavelength followed by the other) cross-correlation relation with a delayed version of the incident waveform. A study of the differential cross-correlation SNR vs. those of two sequential cross-correlations, one at each wavelength, could be employed to show the advantage on imaging quality and threshold blood concentration sensitivity of the differential scheme.

The foregoing embodiments may be employed to: a) enhance photoacoustic imaging contrast; and b) integrate photoacoustic imaging with ultrasound imaging (co-registration). For example, in biological regions where tumors may grow, ultrasound imaging contrast is based on acoustic impedance differences, i.e. differences between the speeds of sound and/or the densities of the lesion and the respective healthy tissue. These same differences can help amplify the differential spectroscopic signals as they will contribute to the cross-correlation difference through the) dependence of the photoacoustic signal on the Grüneisen coefficient, G:

$$G = \frac{\beta c_s^2}{C_p} \tag{20}$$

where $\beta$ is the thermal expansion coefficient (in 1/° C.), $C_p$ is the heat capacity (in J/g° C.), and $c_s$ is the speed of sound in tissue (1.5 mm/μs in normal tissue). Both $c_s$ and $\beta$ may change in abnormal (cancerous) lesions. G multiplies $\mu_a$, thereby possibly amplifying the differential signal.

In summary, the present embodiments disclose modalities of differential spectroscopic photoacoustic radar tissue imaging, whereby frequency-domain photoacoustic radar techniques may be performed that may be superior to the single-ended method described in other embodiments disclosed herein.

In some embodiments, systems and methods are provided for simultaneously interrogating the Hb and $HbO_2$ concentrations in imaged tissues through the acquisition of two spectral cross-correlation images, and their mathematical manipulations, as indicated in Eqs. (18) and (19) to solve for, and obtain, quantitative images of $C_{ox}$ and $C_{de}$ for a) identification of blood rich regions and b) identification of saturated (hypermetabolic) hemoglobin regions where breast (or other) cancer may be diagnosed.

Figure 13:
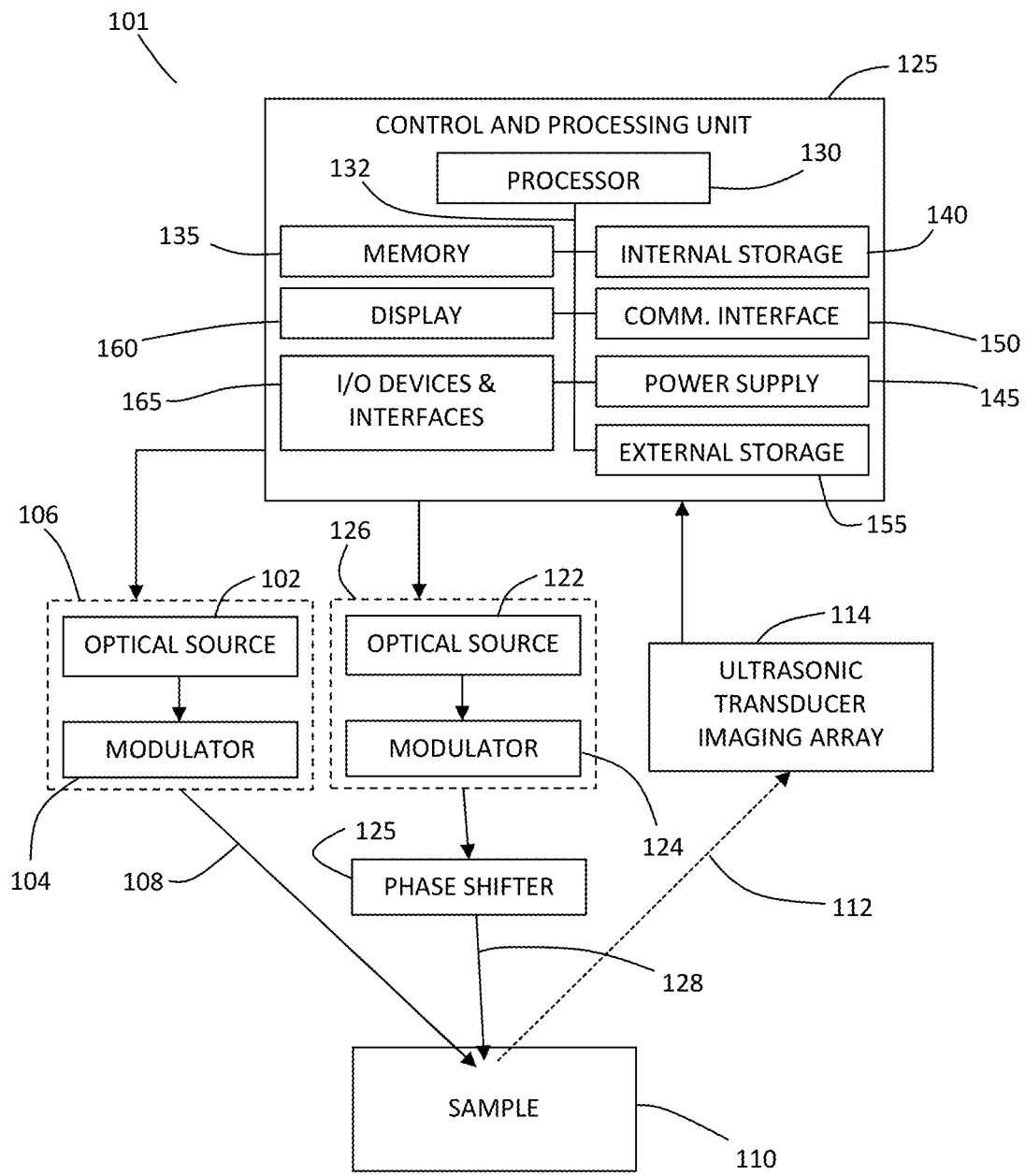
FIG. 13 is a block diagram illustrating an example of a system for performing differential wavelength photoacoustic imaging with a transducer array and correlation image post-processing.

Referring now to FIG. 13, an example apparatus 101 is shown for performing differential photoacoustic cross-correlation imaging. The example apparatus 101 may employ many of the components shown in FIG. 1. In one example implementation, control and processing unit 125 (or one or more external waveform generators 104, 124) generate two simultaneous or sequential approximately out-of-phase modulation waveforms, such as sine wave chirps in the ~1-5 MHz range (or higher, such as 25 MHz). The modulation waveforms modulate the output of first and second optical sources 102 and 122 (such as fast modulatable semiconductor laser diodes). First and second optical sources preferably emit high peak power (such as in the 5-15 W range) sinusoidally or square-wave modulatable CW laser sources) and repetition rate in the 1-10-kHz range (for example, implementable on National Instruments platform).

Control and processing unit 125 may be programmed to implement photoacoustic radar processing steps outlined above. As noted above, the beams emitted by first and second optical sources 102 and 122 are nearly out-of-phase laser-generated ultrasonic chirps. In applications associate with the detection of differences in tissue, one optical source emits a beam having a wavelength (or center wavelength) at approximately the isosbestic wavelength, and the other optical source may emit a beam having a wavelength within the 680-nm range where there exists a local maximum difference in absorption coefficients between $HbO_2$ and Hb (for optimum discrimination between the two types of blood). A maximum output photoacoustic signal may be obtained by adjusting (fine tuning) the phases and amplitudes of the two optical waveforms around the 180-degree point. This is so because the two optical-wave phase difference does not exactly coincide with the generated two-ultrasonic-wave maximum compression and rarefaction phase difference, due to the different optical absorption lengths in the same medium (e.g. blood); in practice, fine tuning around the 180-degree phase shift will be required for maximum differential photoacoustic signal generation.

In another example embodiment, two single-frequency (0.1-30 MHz range) sine-wave or square-wave modulated lasers (modulated out of phase) at, or close to, the isosbestic point (~780 nm) and the other wavelength as described above, simultaneously irradiate the tissue, measuring the photoacoustic signal with at least one ultrasound transducer (an array may be employed for imaging applications). Amplitude- and phase-adjusted waveforms may be used so as to maximize the differential signal due to the different absorption coefficients of a hemoglobin-rich ROI, as described above, with the sign of the relative phase (e.g. the phase of the differential PA signal modulated between 680 nm and 800 nm) indicating the type of lesion (cancerous or benign). The differential method is expected to yield very sensitive and specific photoacoustic imaging contrast when used in a raster scanned mode or with an ultrasonic transducer phase array. This approach, while being disclosed via the example of lesion type detection, may be employed in other applications, in which a sample is characterized by an absorption spectrum possibly, but not necessarily, including an isosbestic point associated with two absorbing species.

The potential amplification of differential photoacoustic signals with regard to healthy tissues based on Grüneisen coefficient contrast superposed on the optical absorption coefficient contrast will further give rise to optimized sensitivity to local tumors excited photoacoustically as discussed in reference to equation 20 above. The following examples are presented to enable those skilled in the art to understand and to practice embodiments of the present disclosure. They should not be considered as a limitation on the scope of the present embodiments, but merely as being illustrative and representative thereof.

EXAMPLES

Example 1

Photoacoustic Imaging with CW Laser Source

The example below illustrates the application of a photoacoustic array imaging system for the imaging of reference sample and human blood vessels. FIG. 7 illustrates the experimental apparatus employed in the present example. A standard ultrasonic 64-element phased array probe 300 was employed (GE Parallel Design, Inc., Phoenix, Ariz.), having a central frequency 3.5 MHz, 80% mean bandwidth at −6 dB and pitch 0.254 mm. The imaging plane is shown in the Figure at 310.

A laser beam 320 was continuously modulated by an acousto-optic modulator (AOM; not shown in Figure) driven by chirp waveforms with linear frequency sweeps in the range of approximately 1-5 MHz (or higher, for example, approximately 1-25 MHz). The laser beam was incident on the sample surface 330 through a container with coupling water at an oblique angle (<20°). The coupling water was in contact with the sample surface through a thin transparent plastic film. The laser spot diameter on the surface was approximately 3 mm and the mean laser power could be varied from 100 mW to 1 W.

Two types of tissue phantoms were prepared for use in the experiments: one was made using PVC plastisol with dispersed $MgO_2$ nanoparticles, and the second utilized water solution of Intralipid™ suspension with concentration 0.24% by volume. Measurements of the scattering coefficient of the PVC phantom using the Monte Carlo technique gave for the reduced scattering coefficient $\mu_s'=4$ cm$^{-1}$ (g=0.9). To simulate an optical heterogeneity, an inclusion with dimensions 1 cm×1 cm×0.5 cm of the same material stained with black color paint (absorption coefficient 4 cm$^{-1}$ at 1064 nm) was inserted into the PVC phantom at depth ~1.5 cm. The liquid phantom contained two inclusions with $\mu_a=2$ and 4 cm$^{-1}$ respectively. The inclusion depth was varied using a micro-positioning stage.

Parallel data acquisition and signal processing were implemented using modular 8-channel analog-to-digit converters (PXI-5105) and LabView software package (National Instruments, Austin, Tex.). The current implementation of the photoacoustic probe did not provide simultaneous acquisition of all 64 channels with high sampling rate. To expedite data collection, a parallel-sequential data collection scheme was developed that utilized parallel readout 340 of a subarray of 8 elements sequentially multiplexed over the entire array using 4 programmable switch boards (PXI-2593). Although such parallel-sequential data acquisition is slower than a truly parallel scheme, it provides an inexpensive and flexible alternative for readout of multiple channels within acceptable time frames. Moreover, the modular PXI architecture permits easy hardware expansion to increase the total number of channels and the size of the parallel subarray, which is important for utilization of various ultrasonic arrays with the photoacoustic probe.

Figure 8:
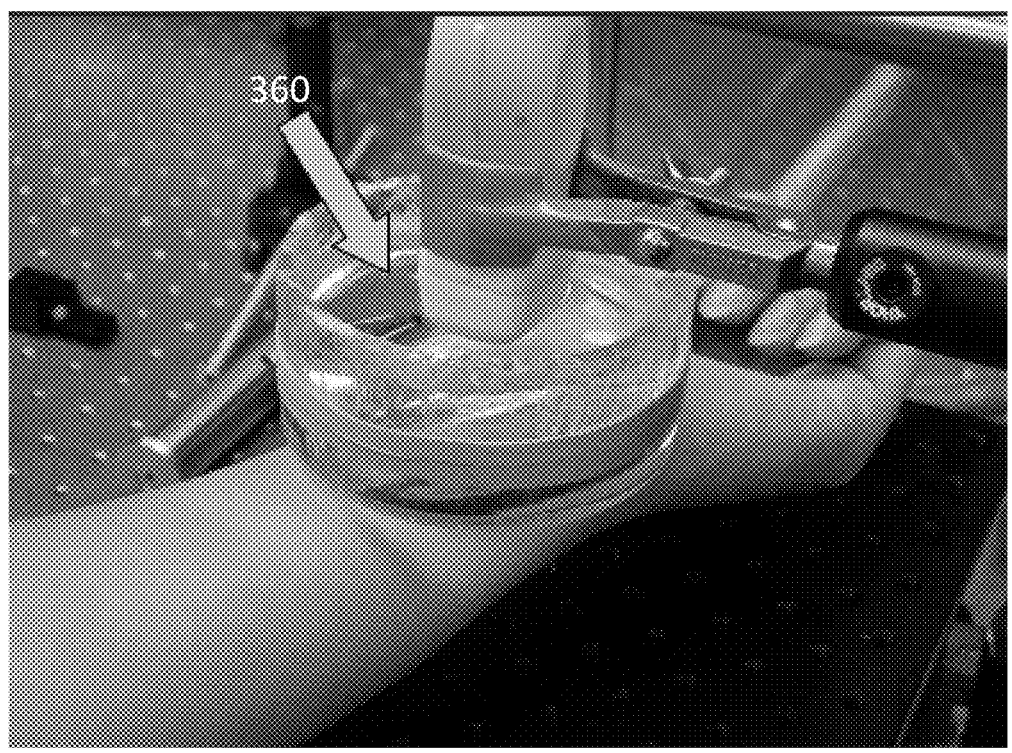
FIG. 8 is a photograph of a system set-up for in-vivo imaging.

Three series of imaging measurements were conducted to verify system performance and its capability to detect optical heterogeneities: first, discrete point-like optical inclusions in the PVC material were imaged to determine spatial resolution of the photoacoustic probe; next, optically scattering (PVC and Intralipid-based) phantoms were employed to image position and size of optical inclusions; and finally, imaging of blood vessels 350 in-vivo was tested using the wrist of a human volunteer, as shown in FIG. 8 (the incident direction of the laser beam is shown at 360).

Initially, the probe point spread function (PSF) was determined using point sources embedded in clear media at different distances from the sensor array. The theoretical PSF shown in FIG. 9(a) was reconstructed using parameters of the transducer array and the frequency-swept point sources positioned at the depth ranging from 1.5 to 6 cm. Gaussian white noise was added to the input signals to simulate detection with SNR=−34 dB.

Figure 9:
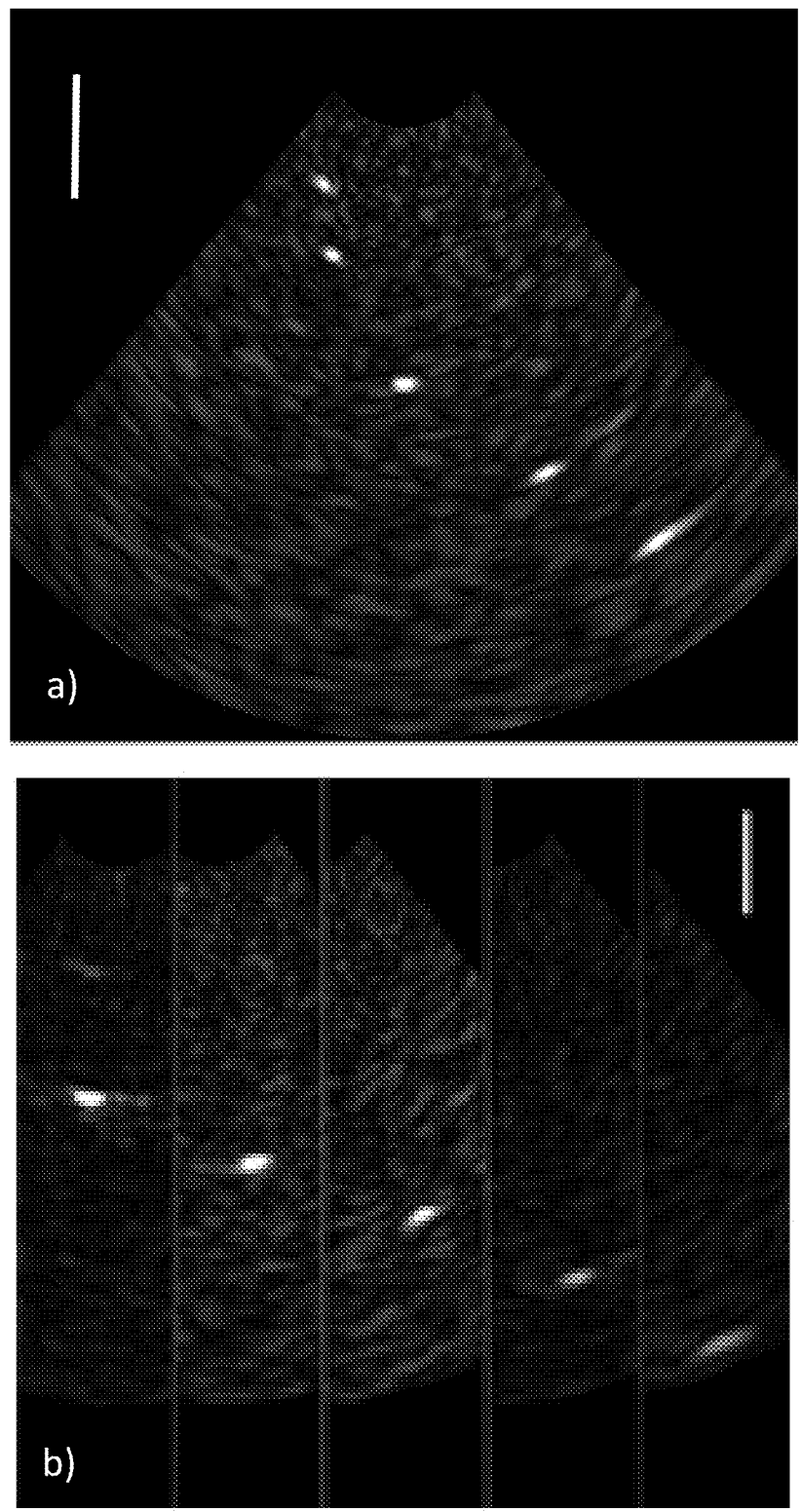
FIG. 9 shows (a) system point spread function (PSF) computed using array parameters and simulated point sources and (b) measured using cotton threads imbedded in a PVC phantom (the vertical scale bar is 1 cm long).

Experimental measurements of the PSF were carried out using five cotton threads positioned at different depths and exposed sequentially to the modulated laser source. Results of the measurements are shown in FIG. 9(b) as a mosaic of five sector scans obtained for the photoacoustic sources positioned at the depths 2-5.5 cm. The results were consistent with the theoretical beam pattern computed for a 64-element array with 0.254 mm pitch.

Figure 10:
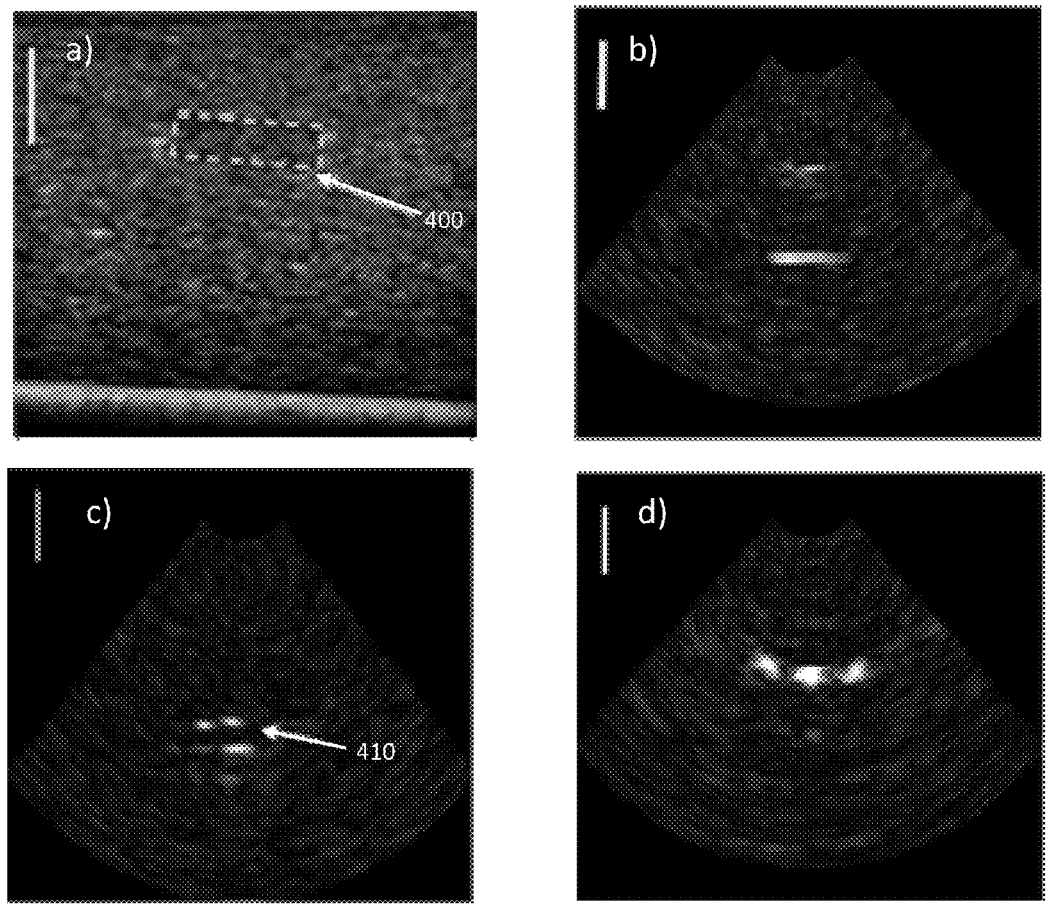
FIG. 10 shows (a) an ultrasound image, (b) a photoacoustic probe image of the PVC phantom with a subsurface inclusion, (c) an image of discrete chromophores immersed in Intralipid™ solution and (d) blood vessels in a human wrist (the vertical scale bar is 1 cm long).

Imaging of optical heterogeneities in the light-scattering media with the photoacoustic probe and coded optical excitation is shown in FIG. 10. Prior to photoacoustic imaging, the PVC phantom was scanned with a conventional ultrasound system (Ultrasonix, British Columbia, Canada) to determine the exact position of the inclusion. The result of the ultrasound test recorded with a 128-element linear probe is shown in FIG. 10(a). Since the inclusion was prepared from the same material, acoustic contrast was negligible and the resulting image contrast was very low.

The inclusion position was identified as an area with slightly reduced speckle density and shown in FIG. 10(a) by a dashed rectangle at 400. On the other hand, imaging the same phantom with the photoacoustic phased array probe, shown in FIG. 10(b), clearly shows optical contrast due to the increased light absorption in the subsurface chromophore and generation of acoustic waves. The upper spot in FIG. 10(b) is due to a laser beam with mean power ~1 W impinging on the surface, while the bright line at the depth 1.5 cm below the surface indicates the top surface of the inclusion.

Similarly, two discrete chromophores immersed in the Intralipid™ solution at 1-cm depth were imaged by the photoacoustic probe. The resulting correlation image, shown in FIG. 10(c), reveals their position and lateral dimensions (shown at arrow 410). The signals observed below the two main peaks correspond to acoustic reflections from the inclusion back surface.

The result of human wrist imaging is shown in FIG. 10(d). The laser beam irradiance of the tissue surface was maintained at <14 W/cm$^2$, which is well below the safety limit of 980 W/cm$^2$ for 1 ms chirp duration. The reconstructed sector image shows discrete bright spots related to sound generation in the superficial blood vessels of the wrist.

An example of dual-mode (ultrasound and photoacoustic) imaging of a tissue specimen ex-vivo with embedded optical contrast heterogeneities (wires) is shown in FIG. 11. A sample of skinless chicken breast tissue with three thin (<200 um) wires inserted at depths 15-20 mm was examined sequentially using a clinical ultrasound scanner SonixTouch (Ultrasonix Inc., Richmond, BC) and photoacoustic radar system. Both imaging systems shared a 64-element phased array brought in contact with the chicken breast through a layer of clear water (2 cm thick) used as a coupling medium.

FIG. 11(a) shows a standard B-mode ultrasonic image with pixel values proportional to the amplitude of backscattered acoustic waves. The three wires in the tissue are labeled with arrows and can be easily identified in the image. Since the tissue structure is highly heterogeneous, strong acoustic speckle is present which reduces the overall image contrast.

The photoacoustic radar image in FIG. 11b was recorded after switching off the normal ultrasound imaging mode, enabling laser irradiation and redirecting signals from the phased array to photoacoustic data acquisition and processing unit as shown in FIG. 1. Optical absorption of wire plastic insulation coating generates acoustic response detected by the phased array. Cross-correlation processing and beamforming applied to the correlation data enables image reconstruction to obtain the cross-correlation image in the same manner as shown in FIG. 11a, but pixel values here are proportional to the amplitude of the cross-correlation signal as opposed to the amplitude of acoustic scattering. Although the physical meaning of the two images is quite different, both indicate the presence of wires and their relative positions. Since chicken breast tissue is optically quite uniform, the background speckle noise is much lower compared to the ultrasound image.

Example 2

Dual Channel, Dual Wavelength Laser Diode Driver Modulator System

In the present example, an example configuration of the optical sources for realizing the apparatus shown in FIG. 13 and for implementing the method shown in FIG. 13 is provided. In the present non-limiting example, first optical source 102 is a 680 nm, 5 watt laser diode, and second optical source 122 is a 780 nm, 5 watt laser diode. An Agilent programmable pulse generator is employed to vary the start and stop frequencies along with sweep rate and continuously variable phase shift between the two channels, for implementing modulators 104, 124, and phase shifter 125 as a single subsystem. The total energy from the pair of laser diodes is coupled to a single 250 to 300 um fiber optic for delivering a single beam to the sample. Each laser diode includes its own thermo-electric cooler with a controller for wavelength stabilization. Each laser diode driver is capable of running at 12 amps at a 50% duty cycle, and the output current of each driver is adjustable. The laser diode drivers have a 25 MHz capability with 30 MHz capability at a reduced output current (~8 amps). The ultimate high end frequency limit is dictated by the inductance of the laser diode package.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A photoacoustic imaging system comprising:
an optical source configured to produce an optical beam;
a modulating means for modulating said optical beam according to a reference modulation waveform and generating a modulated optical beam directed towards a sample;
an ultrasonic transducer array comprising a plurality of elements, wherein each element is configured to detect a photoacoustic wave generated in response to sample absorption of the modulated optical beam, and further configured to generate a photoacoustic signal; and
a control and processing unit operably coupled to at least the modulating means and the ultrasonic transducer array, the control and processing unit configured to:
generate the reference modulation waveform;
calculate, for each element of said ultrasonic transducer array, a cross-correlation function based on a Fourier transform of a generated photoacoustic signal and the reference modulation waveform; and
process the cross-correlation functions in order to generate an image according to a beamforming algorithm, wherein the image represents a spatial distribution of the cross-correlation functions.

2. The photoacoustic imaging system according to claim 1 wherein said optical source is a laser configured for direct current modulation.

3. The photoacoustic imaging system according to claim 2 wherein said laser is a semiconductor laser.

4. The photoacoustic imaging system according to claim 3 wherein said semiconductor laser has a modulation bandwidth within the range of MHz to 25 MHz and a full chirp repetition rate within the range of 1 kHz to 10 kHz.

5. The photoacoustic imaging system according to claim 1 wherein a wavelength of said optical beam is within the range of 755 nm to 808 nm.

6. The photoacoustic imaging system according to claim 1 wherein an electrical connection between said ultrasonic transducer array and said control and processing unit is a parallel electrical connection.

7. The photoacoustic imaging system according to claim 6 wherein said control and processing unit is further configured to process the photoacoustic signals from said ultrasonic transducer array in parallel.

8. The photoacoustic imaging system according to claim 1 wherein the sample is tissue, wherein said optical source is configured to provide a maximum surface irradiance, and wherein the reference modulation waveform is a chirped waveform, and wherein a duration of the chirp of the reference modulation waveform is provided such that a maximum permissible exposure criteria for the tissue is met.

9. The photoacoustic imaging system according to claim 1 wherein a power of said optical source exceeds 10 W.

10. The photoacoustic imaging system according to claim 1 wherein a wavelength of said optical beam is a first wavelength and said reference modulation waveform is a first reference modulation waveform;
wherein said system further comprises a second optical source for producing a second optical beam; and
wherein said modulating means is adapted for modulating said second optical beam according to a second reference modulation waveform and generating a second modulated optical beam.

11. The photoacoustic imaging system according to claim 10;
wherein said first wavelength is approximately equal to a wavelength of an isosbestic point of oxyhemoglobin and deoxyhemoglobin, and a wavelength of said second optical source is a second wavelength and is a wavelength other than said first wavelength; and
wherein said second reference modulation waveform differs by said first reference modulation waveform by a phase shift of approximately 180 degrees.

12. The photoacoustic imaging system according to claim 1 wherein said second wavelength is approximately equal to 680 nm.

13. The photoacoustic imaging system according to claim 10 wherein said control and processing unit is further configured to:
generate the second reference modulation waveform;
calculate, for each element of said ultrasonic transducer array, a second cross-correlation function based on a Fourier transform of a generated photoacoustic signal and the second reference modulation waveform; and
process the second cross-correlation functions in order to generate an image according to a beamforming algorithm, wherein the image represents a spatial distribution of the cross-correlation functions.

14. The photoacoustic imaging system according to claim 1 further comprising an ultrasound source for generating a modulated ultrasonic beam and spatially overlapping the modulated ultrasonic beam with the optical beam at a region of interest within the sample, wherein the modulated ultrasonic beam is modulated according to the reference modulation waveform, and wherein a phase relationship between the modulated optical beam and the modulated ultrasonic beam is selected to enhance the photoacoustic signal.

15. The photoacoustic imaging system according to claim 14 wherein the ultrasound source is a high intensity focused ultrasound transducer.

16. A method of performing differential photoacoustic imaging on a sample, wherein an absorption spectrum of the sample includes an isosbestic point associated with oxyhemoglobin and deoxyhemoglobin, the method comprising:

providing a first optical beam having a first wavelength, wherein the first wavelength is approximately equal to a wavelength of the isosbestic point of oxyhemoglobin and deoxyhemoglobin;

providing a second optical beam having a second wavelength, wherein the second wavelength is different than the first wavelength;

generating a reference modulation waveform;

modulating the first optical beam and the second optical beam according to the reference modulation waveform, thereby obtaining a first modulated optical beam and a second modulated optical beam, wherein the first modulated optical beam and the second modulated optical beam are approximately out of phase;

directing the first modulated optical beam and the second modulated optical beam onto the sample;

detecting, with an ultrasonic transducer array comprising a plurality of elements, photoacoustic waves responsively generated within the sample and obtaining a differential photoacoustic signal from each element of the ultrasonic transducer array;

calculating, using a processor, for each element of said ultrasonic transducer array, a cross-correlation function based on a Fourier transform of a generated photoacoustic signal and the reference modulation waveform; and processing, using the processor, the cross-correlation functions in order to generate an image according to a beamforming algorithm, wherein the image represents a spatial distribution of the cross-correlation functions.

17. The method according to claim 16 further comprising inferring a property of the sample based on the sign of the phase of the differential photoacoustic signal.

18. The method according to claim 17 wherein the property is a characterization of a tumor.

19. The method according to claim 17 wherein the property is a degree of oxygenation of blood within the sample, wherein the sample comprises a tissue.

* * * * *